United States Patent
Zhou et al.

(10) Patent No.: US 9,212,055 B2
(45) Date of Patent: Dec. 15, 2015

(54) ALIGNED, COATED NANOWIRE ARRAYS FOR GAS SENSING

(76) Inventors: Weilie Zhou, New Orleans, LA (US); Jiajun Chen, Guangdong (CN); Kai Wang, New Orleans, LA (US)

(*) Notice: Subject to any disclaimer, the term of this patent is extended or adjusted under 35 U.S.C. 154(b) by 0 days.

(21) Appl. No.: 13/245,138

(22) Filed: Sep. 26, 2011

(65) Prior Publication Data

US 2012/0097917 A1 Apr. 26, 2012

Related U.S. Application Data

(60) Provisional application No. 61/387,540, filed on Sep. 29, 2010.

(51) Int. Cl.
| | |
|---|---|
| *B82Y 15/00* | (2011.01) |
| *B82Y 40/00* | (2011.01) |
| *G01N 27/12* | (2006.01) |
| *H01L 29/06* | (2006.01) |

(52) U.S. Cl.
CPC ............... *B82Y 15/00* (2013.01); *B82Y 40/00* (2013.01); *G01N 27/127* (2013.01); *H01L 29/0676* (2013.01)

(58) Field of Classification Search
CPC ....... B82Y 15/00; B82Y 40/00; G01N 27/127
USPC .................................. 977/953, 957, 762, 811
See application file for complete search history.

(56) References Cited

U.S. PATENT DOCUMENTS

| 7,569,905 B2 * | 8/2009 | Hantschel et al. ............ 257/475 |
| 2007/0194467 A1 * | 8/2007 | Yang et al. ............ 257/E23.155 |
| 2010/0012919 A1 * | 1/2010 | Park et al. ......................... 257/9 |
| 2010/0112349 A1 * | 5/2010 | Su et al. ....................... 428/389 |

OTHER PUBLICATIONS

Law et al., ZnO—Al2O3 and ZnO—TiO2 Core-Shell Nanowire Dye-Sensitized Solar Cells,2006,J.Phys. Chem. B, 110, 22652-22663.*
Cao, B. et al., "Growth of monoclinic $WO_3$ nanowire array for highly sensitive $NO_2$ detection," *J. Mat. Chem.*, vol. 19, pp. 2323-2327 (2009).
Chen, J. et al., "Facile Route to Polycrystalline Pd/SnO2 Nanowires Using ZnO-Nanowire Templates for Gas-Sensing Applications," *IEEE Trans. Nanotechnology*, vol. 9, pp. 634-639 (2010).
Chen, J. et al., "$H_2S$ Detection by Vertically Aligned CuO Nanowire Array Sensors," *J. Phys. Chem. C*, vol. 112, pp. 16017-16021 (2008).
Chen, J. et al., "Highly Sensitive and Selective Gas Detection by 3D Metal Oxide Nanoarchitectures," pp. 391-412 in W. Zhou et al. (Eds.), *Three-Dimensional Nanoarchitectures* (Springer Science-Business Media, New York 2011).

(Continued)

*Primary Examiner* — Jose R Diaz
(74) *Attorney, Agent, or Firm* — John H. Runnels

(57) ABSTRACT

Aligned nanowire arrays were coated with semiconductor shell layers, and optionally with noble metal nanoparticles for use as three dimensional gas sensors. The sensors show room-temperature responses to low concentrations of various gases. Arrays containing different sensor types can discriminate among different gases, based upon changes in conductivity and response times.

3 Claims, 26 Drawing Sheets

(56) References Cited

OTHER PUBLICATIONS

Chen, J. et al., "Vertically aligned ZnO nanorod arrays coated with $SnO_2$ / noble metal nanoparticles for highly sensitive and selective gas detection," *IEEE Trans. Nanotechnology*, vol. 10, pp. 968-974 (2011).

Chen, J. et al., "Well-Aligned Metal Oxide Nanowire Arrays for Highly Sensitive and Selective Gas Detection," Abstract, 2009 Nanoelectronic Devices for Defense & Security Conference (Fort Lauderdale, Florida, Sep. 28-Oct. 2, 2009).

Chen, J., *Highly Sensitive and Selective Gas Sensors Based on Vertically Aligned Metal Oxide Nanowire Arrays*, PhD Dissertation (University of New Orleans, Dec. 2010).

Chen, P. et al., "A nanoelectronic nose: a hybrid nanowire/carbon nanotube sensor array with integrated micromachined hotplates for sensitive gas discrimination," *Nanotechnology*, vol. 20, pp. 125503-125510 (2009).

Chen, Z. et al., "Silicon-induced oriented ZnS nanobelts for hydrogen sensitivity," *Nanotechnology*, vol. 19, pp. 055710-055714 (2008).

Johnson, J. et al.,"Growth and Characterization of GaN Nanowires for Hydrogen Sensors," *J. Elec. Mater.*, vol. 38, pp. 490-494 (2009).

Kolmakov, A. et al., "Enhanced Gas Sensing by Individual $SnO_2$ Nanowires and Nanobelts Functionalized with Pd Catalyst Particles," *Nano Letters*, vol. 5, pp. 667-673 (200.

Star, A. et al., "Gas Sensor Array Based on Metal-Decorated Carbon Nanotubes," *J. Phys. Chem. B*, vol. 110, pp. 21014-2020 (2006).

Sysoev, V. et al., "Toward the Nanoscopic 'Electronic Nose': Hydrogen vs Carbon Monoxide Discrimination with an Array of Individual Metal Oxide Nano- and Mesowire Sensors," *Nano Letters*, vol. 6, pp. 1584-1588 (2006).

Su, H. et al., "Different Metal Oxides Modified ZnO Nanowire Arrays for Highly Sensitive and Selective Gas Detection," Abstract, 2011 Nanoelectronic Devices for Defense & Security Conference (New York, Aug. 26-Sep. 1, 2011).

\* cited by examiner

ALIGNED, COATED NANOWIRE ARRAYS FOR GAS SENSING

The benefit of the Sep. 29, 2010 filing date of U.S. provisional patent application Ser. No. 61/387,540 is claimed under 35 U.S.C. §119(e) in the United States, and is claimed under applicable treaties and conventions in all countries.

This invention was made with government support under grant HR0011-07-1-0032 awarded by the Defense Advanced Research Projects Agency. The United States Government has certain rights in this invention.

This invention pertains to nanowire arrays, and to the use of such arrays in the detection of gases.

Gas sensors are important in many applications, such as chemical engineering, environmental monitoring, medical diagnostics, industrial safety, and public security. There is an ongoing, unfilled need for improved, highly sensitive, and selective gas detection devices. Prior gas sensing devices have been based upon various types of detectors, including surface acoustic wave detectors, micromachined cantilevers, conducting polymer sensors, and metal oxide conductometric sensors. Metal oxide conductometric gas sensors are probably most widely used due to their low fabrication cost, high stability, and sensitivity.

More recently, sensitive and selective gas sensors have been developed using metal oxide nanowires as active elements. The metal oxide nanowires have advantageous intrinsic properties including high surface-to-volume ratio, and feature sizes on the order of a typical Debye length for a gas molecule. Metal oxide nanowires have been fabricated with catalytic metal decoration or other surface functionalizations to modify or otherwise improve sensitivity. To improve selectivity, efforts have focused on developing materials that response specifically to a particular gas of interest, sometimes called the "lock-and-key" approach. Nanosensor arrays have been formed from different one-dimensional lateral nanostructures or nanowires having different catalytic decorations, with broad cross-reactivities, to discriminate between various environmental or industrial gases.

ZnO nanowires have been studied intensively. Various synthesis are known for fabricating vertically aligned ZnO nanowires with high reproducibility and alignment. More generally, however, there remains an unfilled need for general routes to prepare vertically aligned metal oxide nanowire arrays to facilitate the fabrication of three-dimensional devices from a wider array of materials.

A. Kolmakov et al., "Enhanced Gas Sensing by Individual $SnO_2$ Nanowires and Nanobelts Functionalized with Pd Catalyst Particles," *Nano Letters*, vol. 5, pp. 667-673 (2005) discloses measurements on individual $SnO_2$ nanowires and nanobelts functionalized with palladium catalyst particles, and their use as gas sensors for oxygen and hydrogen. Gold was used in some experiments in lieu of palladium.

A. Star et al., "Gas Sensor Array Based on Metal-Decorated Carbon Nanotubes," *J. Phys. Chem. B*, vol. 110, pp. 21014-21020 (2006) discloses the use of single-walled carbon nanotubes decorated with one of eighteen different catalytic metals (Mg, Al, Ti, V, Cr, Mn, Fe, Co, Ni, Zn, Mo, Rh, Pd, Sn, W, Pt, Au, and Pb) for the detection of $H_2$, $CH_4$, CO, and $H_2S$ gases. A sensor array was fabricated by electroplating Pd, Pt, Rh, and Au onto isolated carbon nanotube networks on a single chip, and tested for the detection of $H_2$, $CH_4$, CO, $NO_2$ and $H_2S$ gases.

V. Sysoev et al., "Toward the Nanoscopic 'Electronic Nose': Hydrogen vs Carbon Monoxide Discrimination with an Array of Individual Metal Oxide Nano- and Mesowire Sensors," *Nano Letters*, vol. 6, pp. 1584-1588 (2006) discloses arrays of chemiresistors made of individual pristine $SnO_2$, surface doped (Ni)—$SnO_2$ nanowires, and $TiO_2$ and $In_2O_3$ mesoscopic whiskers, and their use as gas sensors for oxygen, hydrogen, and carbon monoxide. A three-chemiresistor array was used to discriminate between $H_2$ and CO gases.

P. Chen et al., "A nanoelectronic nose: a hybrid nanowire/carbon nanotube sensor array with integrated micromachined hotplates for sensitive gas discrimination," *Nanotechnology*, vol. 20, pp. 125503-125510 (2009) discloses a chemical sensor array composed of individual $In_2O_3$ nanowires, $SnO_2$ nanowires, ZnO nanowires, and single-walled carbon nanotubes with integrated micromachined hotplates for gas discrimination. Principal component analysis was used for pattern recognition. The array was used to detect hydrogen, ethanol, and nitrogen dioxide at different concentrations and sensing temperatures. The temperatures of the sensors could be individually controlled up to 350° C. $NO_2$ was detected both at room temperature and at 200° C. Neither $H_2$ nor ethanol was detected at room temperature, while both were detected at 200° C.

J. Chen et al., "$H_2S$ Detection by Vertically Aligned CuO Nanowire Array Sensors," *J. Phys. Chem. C*, vol. 112, pp. 16017-16021 (2008) discloses chemical sensors based on vertically aligned CuO nanowire arrays, capable of detecting diluted $H_2S$. The sensor demonstrated strong selectivity for $H_2S$, as compared with the responses to high concentrations of $H_2$, CO, and $NH_3$.

B. Cao et al., "Growth of monoclinic $WO_3$ nanowire array for highly sensitive $NO_2$ detection," *J. Mat. Chem.*, vol. 19, pp. 2323-2327 (2009) discloses the preparation of a $WO_3$ nanowire array, and its use in the detection of $NO_2$ gas.

Z. Chen et al., "Silicon-induced oriented ZnS nanobelts for hydrogen sensitivity," *Nanotechnology*, vol. 19, pp. 055710-055714 (2008) discloses the fabrication of oriented ZnS nanobelts, and their use in sensing hydrogen gas.

J. Johnson et al., "Growth and Characterization of GaN Nanowires for Hydrogen Sensors," *J. Elec. Mater.*, vol. 38, pp. 490-494 (2009) discloses the fabrication of GaN nanowires, and their use in sensing hydrogen gas.

Related work by the present inventors and their colleagues, not believed to be prior art to the present invention, is disclosed in: J. Chen et al., "Well-Aligned Metal Oxide Nanowire Arrays for Highly Sensitive and Selective Gas Detection," Abstract, 2009 Nanoelectronic Devices for Defense & Security Conference (Fort Lauderdale, Fla., Sep. 28-Oct. 2, 2009); J. Chen et al., "Facile Route to Polycrystalline Pd/SnO2 Nanowires Using ZnO-Nanowire Templates for Gas-Sensing Applications," *IEEE Trans. Nanotechnology*, vol. 9, pp. 634-639 (2010); J. Chen et al., "Vertically aligned ZnO nanorod arrays coated with $SnO_2$/noble metal nanoparticles for highly sensitive and selective gas detection," *IEEE Trans. Nanotechnology*, vol. 10, pp. 968-974 (2011); J. Chen, *Highly Sensitive and Selective Gas Sensors Based on Vertically Aligned Metal Oxide Nanowire Arrays*, PhD Dissertation (University of New Orleans, December 2010); and J. Chen et al., "Highly Sensitive and Selective Gas Detection by 3D Metal Oxide Nanoarchitectures," pp. 391-412 in W. Zhou et al. (Eds.), Three-Dimensional Nanoarchitectures (Springer Science-Business Media, New York 2011); H. Su et al., "Different Metal Oxides Modified ZnO Nanowire Arrays for Highly Sensitive and Selective Gas Detection," Abstract, 2011 Nanoelectronic Devices for Defense & Security Conference (New York, Aug. 26-Sep. 1, 2011).

It remains true that no artificial sensor can out-compete a dog's nose for sensitivity, response time, selectivity, and directional tracking. The canine olfactory system comprises hundreds of millions of receptors, each several hundred nanometers in diameter and several micrometers long, providing tremendous surface area and chemical diversity for highly sensitive and selective detection. Our work was inspired in part by the canine olfactory receptor system.

We have discovered novel gas sensors fabricated from vertically-aligned metal oxide nanowire arrays. The arrays have successfully detected a number of gases, including both $H_2S$ and $NO_2$ at the ppb level at room temperature. Nanowire arrays formed from a metal oxide, such as ZnO, are used as structural templates. The structural templates support a "shell layer," a highly sensitive nanoparticle coating of semiconductor, for example a metal oxide such as $SnO_2$, that responds to the presence of one or more gases. Optionally, noble metal nanoparticles are also added to the shell layer to further enhance sensitivity, and to tune responsiveness to different gases. Arrays of multiple sensors having different compositions, e.g. having different noble metal decorations within the shell layer, can be used to enhance the ability to discriminate between different gases. A prototype array with three different noble metal decorations has been used to discriminate between the air-diluted gases $NO_2$, $H_2S$, $NH_3$, CO, and $H_2$.

A typical response time with the novel device is on the order of tens of seconds, similar to that of existing commercial sensors. The novel device can operate at lower temperatures, typically room temperature, which allows substantially reduced power consumption and facilitates portable applications.

BRIEF DESCRIPTION OF THE DRAWINGS

FIG. 6 depicts measurements for $NO_2$. FIG. 7 depicts measurements for $H_2S$. FIG. 8 depicts measurements for $H_2$. FIG. 9 depicts measurements for CO. FIG. 10 depicts measurements for $NH_3$.

FIG. 11(a) depicts detection of $H_2$. FIG. 11(b) depicts detection of CO. FIG. 11(c) depicts detection of $NH_3$. FIG. 11(d) depicts a principal component analysis of measurements with five gases.

EXAMPLE 1

Fabrication of ZnO Nanowire Arrays

Figure 1A:
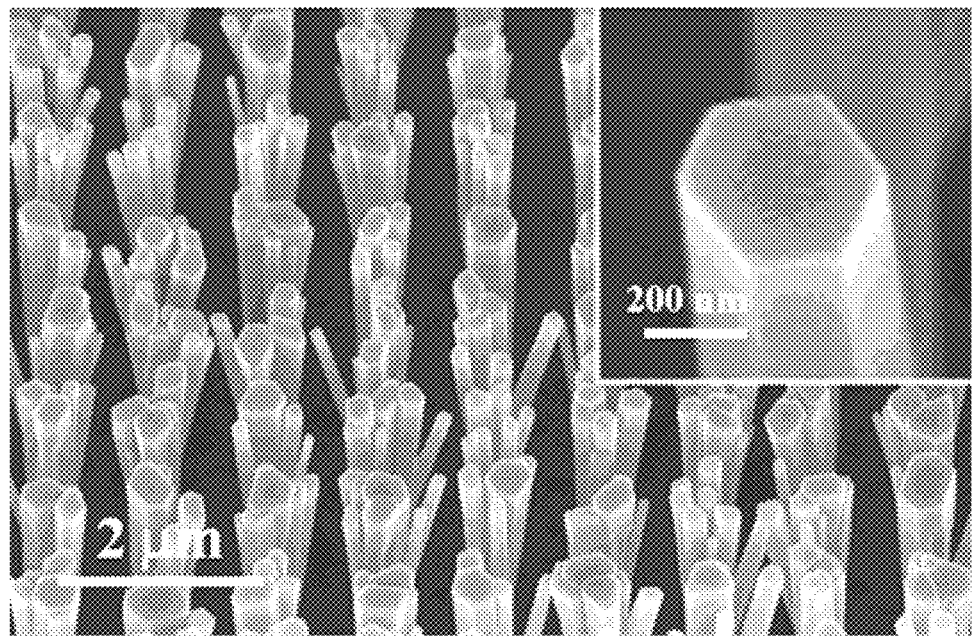
FIGS. 1(a) and 1(b) depict, respectively, FESEM images of a ZnO nanowire array, and a nanowire array with $SnO_2$ and noble metal nanoparticle coatings.

A ZnO nanowire array for gas sensors was prepared as follows. A 5×5 mm² thermally-oxidized Si substrate was ultrasonically cleaned with acetone, isopropanol, and deionized water. After cleaning, the substrate was dried under nitrogen.

The dried substrate was loaded into a Cressington 308R thin-film coating system to receive a bottom electrode coating. A 10 nm Cr film was first coated by direct current sputtering at room temperature to ensure adhesion between the amorphous silicon oxide and the succeeding gold layer. Subsequently, a 20 nm Au layer was coated onto the Cr layer by direct current sputtering at room temperature.

The substrate with the Cr and Au layers was then coated with a 5 nm amorphous ZnO layer at room temperature by radio frequency sputtering in a Lesker PVD 75 system. The deposition rate was maintained in the range of 0.2~0.4 Angstrom/second. A "nutrition solution" having a 1:1 mass ratio of $Zn(NO_3)_2$ to hexamethylenetetramine was prepared and stirred for 24 hours. The concentrations of the nutrition solution, for preparing a textured seed layer and for inducing nanowire growth, were 25 mmol/L and 5 mmol/L, respectively. The substrate was flipped upside-down and floated upon the nutrition solution to inhibit precipitate deposition and overgrowth. The seed layer was grown at 90° C. for 2 hours. Structural analysis of the as-grown seed layer is given in Figures S1 and S2 of the supporting information, which appears in Appendix A of priority application Ser. No. 61/387,540. The substrate was then cleaned with isopropanol and deionized water, and dried under nitrogen.

Before the e-beam lithography process, a layer of poly (methyl methacrylate) (PMMA) (Microchem, 950A4) was spin-coated at 3000 rpm, and then post-heated at 150° C. for 90 seconds. The patterns were exposed with a 10 kV electron beam in a Carl Zeiss 1530 variable-pressure field emission scanning electron microscope (FESEM). Scanning was controlled by a nanopattern generation system attached to the microscope. The exposed PMMA was then developed by developer solution (3 parts isopropanol-1 part methyl isobutyl ketone (v:v)) for 75 seconds, and subsequently washed in isopropanol and de-ionized water for 1 minute. The substrate was then dried under nitrogen. An example of patterned PMMA is shown in Figure S3 of the supporting information (cited above). The pattern used in the embodiment depicted in Figure S3 was a square array of ϕ 300 nm windows, with a 1 micron window-to-window distance.

A ZnO nanowire array was grown at 90° C. for 12 hours in a 5 mmol/L nutrition solution by hydrothermal growth. Following growth, the PMMA layer was removed with acetone. The as-grown nanowire array was dried at 80° C. in a convection oven.

EXAMPLE 2

Coating the ZnO Nanowire Array with $SnO_2$ Nanoparticles, and Optionally with Noble Metal Nanoparticles Also A 50 nm $SnO_2$ nanoparticle layer was then coated onto the entire nanowire array by radio frequency sputtering at a deposition rate of 0.5 Angstrom/second at 200° C. Optionally, noble metal particles were sputtered onto the nanowire arrays after the $SnO_2$ nanoparticle layer under similar conditions, with a "normalized thickness" of 0.5 nm. (Because the noble metal formed discrete particles rather than a continuous film, the "thickness" is not well-defined. What we have called the "normalized thickness" is simply the thickness of the noble metal as measured by the thickness monitor, measurements that assumed the noble metal formed a continuous film on the $SnO_2$ surface.) The structure and composition of the nanowires was checked both by FESEM and by a JEOL 2010 transmission electron microscope equipped with a x-ray energy dispersive spectroscope.

EXAMPLE 3

Testing I-V Characteristics of the Devices

To test the sensing performance of the sensors, the sensors were loaded into a purpose-built testing chamber. The current-voltage (I-V) characteristics of each device were first measured before the sensor testing and the conductance of each device was continuously recorded by a Keithley 2400 source meter incorporated with 7001 switch modules, as various air-diluted gases were sent into the testing chamber. The gas sensors were restored between tests by flushing the chamber with dry air.

EXAMPLES 4-8

Figure 1B:
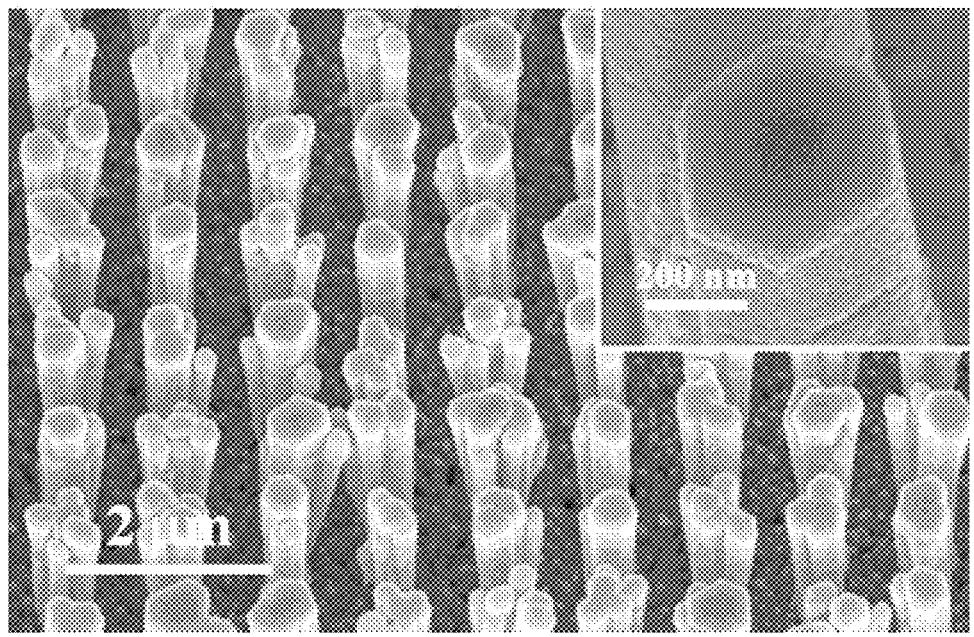

Electron Micrograph and Electron Diffraction Pattern Studies of ZnO Nanowire Arrays, with and without Nanoparticle Coatings FIGS. 1(a) and 1(b) depict, respectively, FESEM images of a ZnO nanowire array prepared as described above, and a nanowire array with $SnO_2$ and noble metal nanoparticle coatings. The diameters of the pristine ZnO nanowires were 150~450 nm. We observed that multiple nanowires often grew from a single window, which we attributed to the presence of several textured ZnO seeds within a single PMMA "window," (which we also observed by FESEM). Some nanowires had diameters larger than the pattern size (~300 nm), indicating that some lateral growth had occurred. Magnified views of the nanowire tips showed surface roughness changes following the nanoparticle coating, consistent with essentially complete coverage by the $SnO_2$ nanoparticles.

The overall morphology observed by FESEM confirmed that hydrothermal growth, combined with e-beam patterning, allowed precision control of the growth of the ZnO nanowires. FIGS. 1(c), 1(d), and 1(e) from priority application Ser. No. 61/387,540 (not duplicated here, but incorporated by reference) depict transmission electron microscopy structural and composition analyses of a ZnO nanowire coated with $SnO_2$ and Pd nanoparticles. The $SnO_2$ surface coating comprised tilted column structures interspersed with empty channels. The $SnO_2$ particles had an irregular shape, with diameters about 15~20 nm. This growth of column structures may have resulted from the grazing angle between the incident deposition source and the nanowire sidewalls. It is possible that the columnar structure may be beneficial to sensor performance, by permitting gas molecules to diffuse in or to be released readily. FIG. 1(d) from the priority application depicts a selected area electron diffraction pattern along the ZnO [0 1 $\bar{1}$ 0] zone on a nanowire, showing c-axis growth of the ZnO nanowire, a pattern that is in agreement with the hexagonal shape observed under FESEM. Furthermore, the observed ring patterns appeared to be generally consistent with those of rutile $SnO_2$. An energy dispersive x-ray spectrum, depicted in FIG. 1(e) from the priority application, further confirmed that the ZnO nanowires had been coated with $SnO_2$ and Pd nanoparticles.

EXAMPLES 9 and 10

Pt or Au Nanoparticle Coatings

In alternative embodiments, in place of the Pd nanoparticles, Pt and Au were used as catalytic metals, otherwise following the same fabrication procedures.

Without wishing to be bound by this hypothesis, it is believed that the noble metal nanoparticles can effectively pre-dissociate the gas molecules into atomic species; and further, that the catalytic behaviors of different noble metals are different. Accordingly, the pre-dissociations induced by the noble metal decorations not only act to increase sensor sensitivity, but also to modify the device characteristics. Selectivity can be further enhanced by using an array of sensors having different noble metal decorations, and therefore different responses to different gas molecules.

EXAMPLE 11

Electron Micrographs of Steps in the Fabrication Process

Figure 2A:
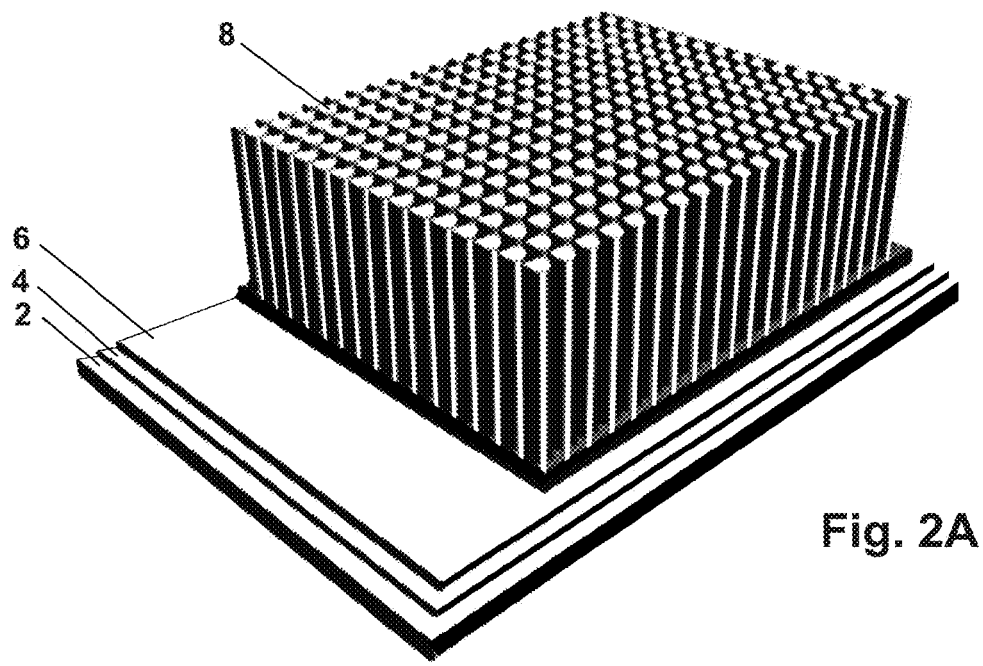
FIGS. 2(a) through 2(d) depict the fabrication process for top electrodes schematically.
Figure 2B:
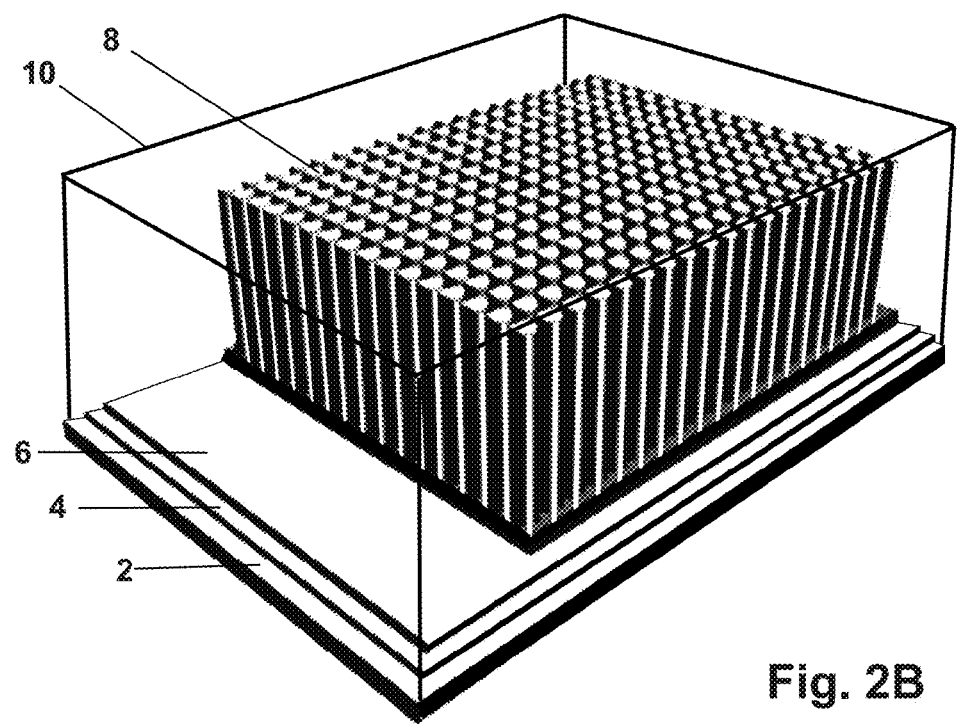
Figure 2C:
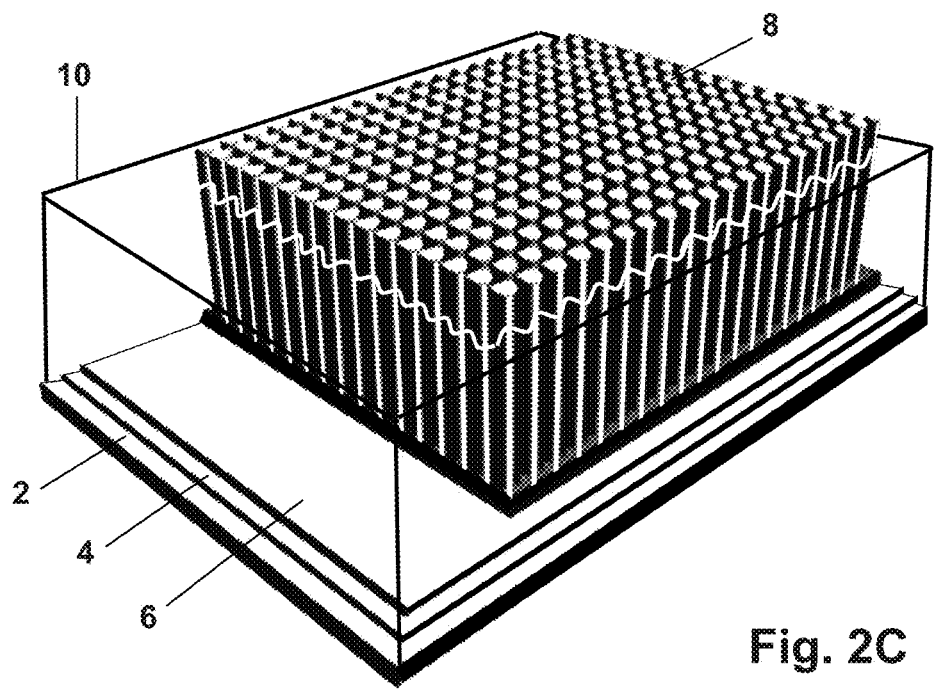
Figure 2D:
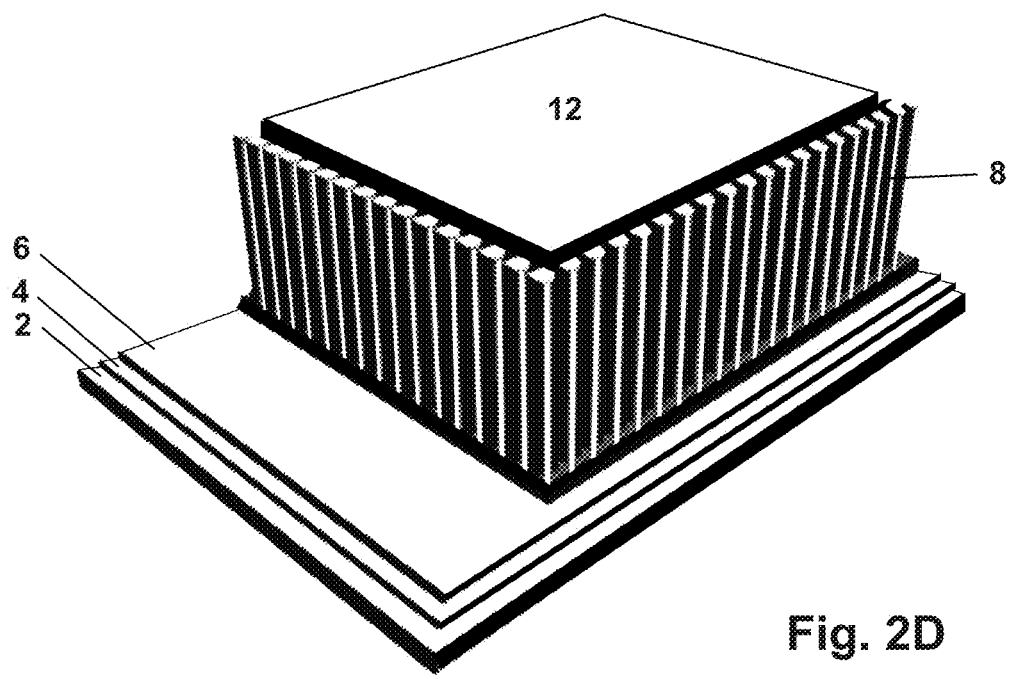
Figure 2E:
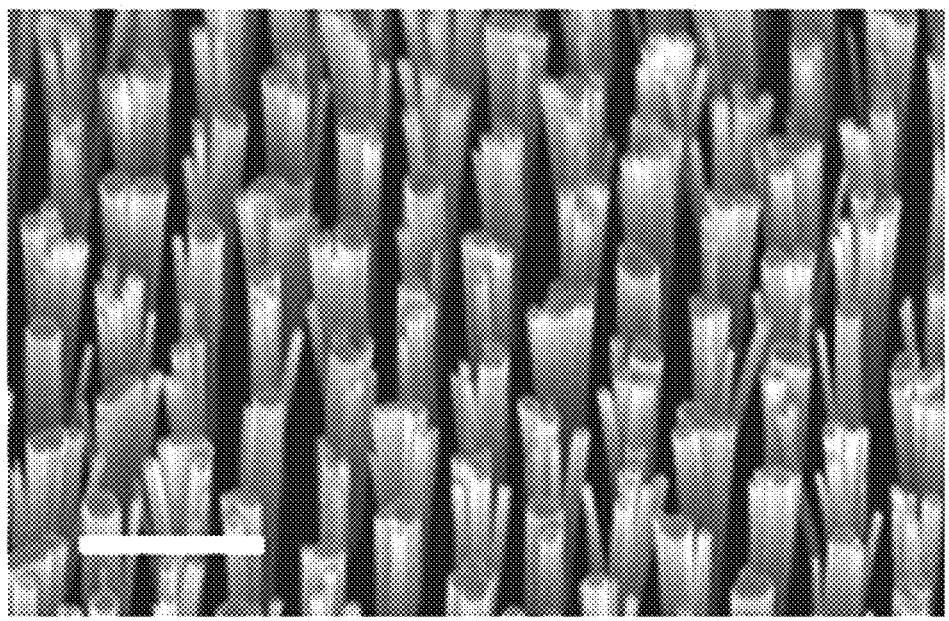
FIGS. 2(e) through 2(h) depict corresponding FESEM images.
Figure 2F:
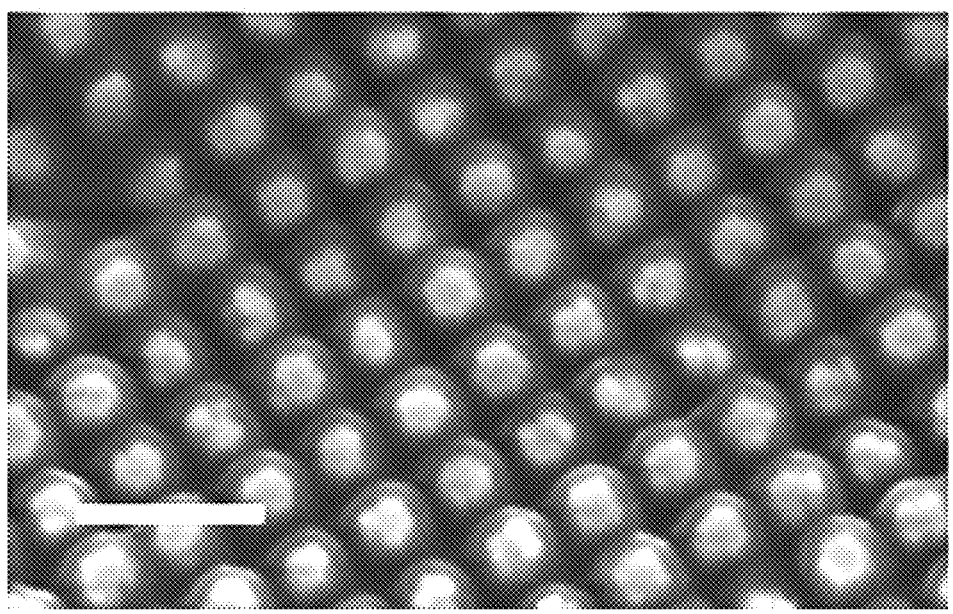
Figure 2G:
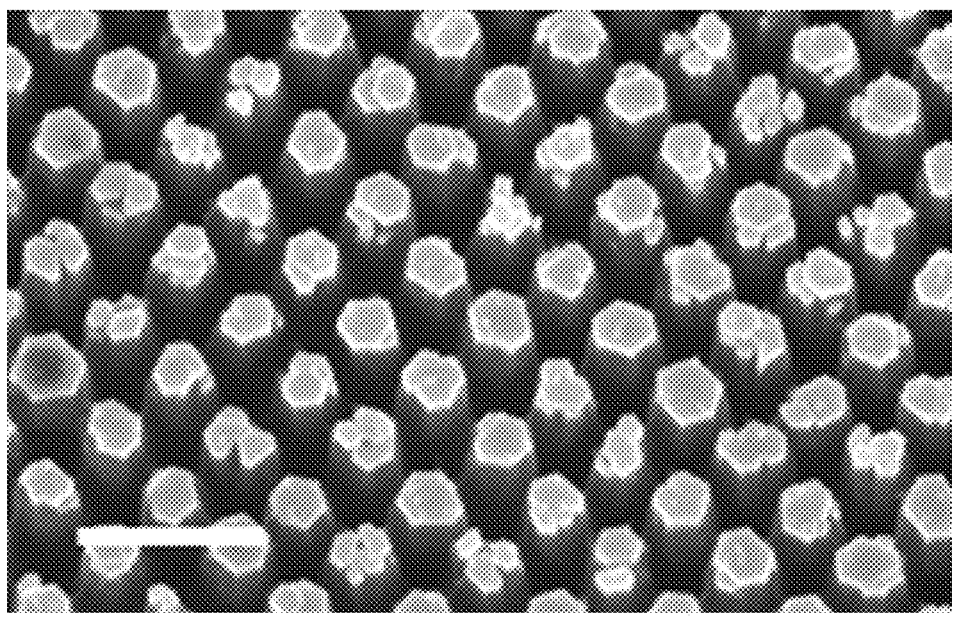
Figure 2H:
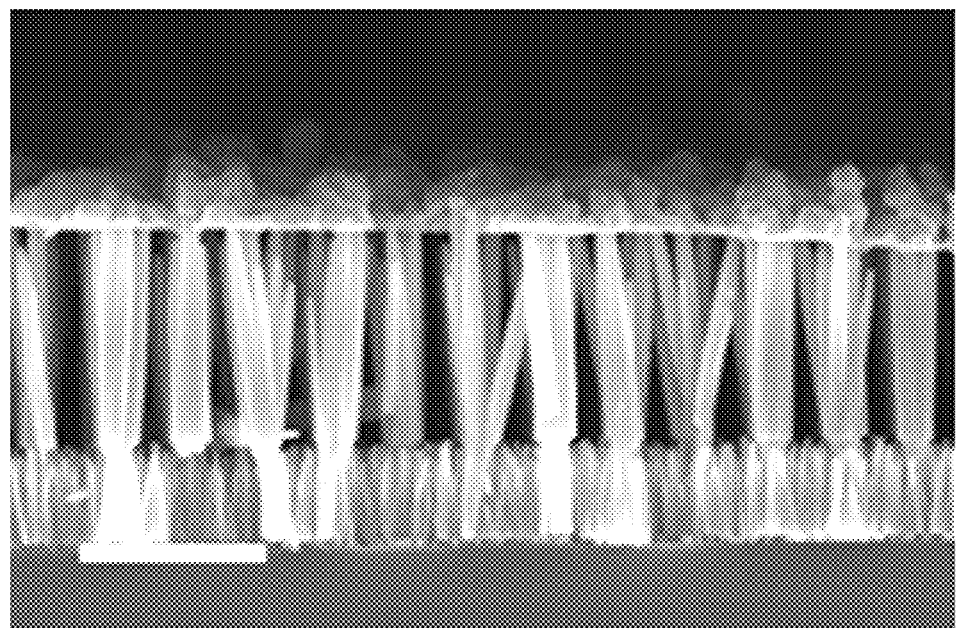

FIGS. 2(a) through 2(d) depict the fabrication process for top electrodes schematically, and FIGS. 2(e) through 2(h) depict corresponding FESEM images; scale bars are 2 micrometers. Silicon substrate 2 was coated with Cr layer 4 and Au layer 6. A ZnO nanowire array 8, coated with $SnO_2$/noble metal (Pd, Pt, or Au) nanoparticles, was formed on Au layer 6 as shown in FIGS. 2(a) and 2(e). The entire array was covered with a layer of PMMA 10 (Microchem, 950A4) by spin-coating at a rotation rate of 500 rpm. See FIGS. 2(b) and 2(f). As shown in FIGS. 2(c) and 2(g), the tips of nanowires 8 were then exposed by etching the PMMA layer 10 with an oxygen plasma (100 W, SPI Plasma Prep II) at a rate of 80 nm/min. A 100 nm Au layer 12 was then sputtered as the top electrode, the 2 mm×2 mm dimensions of which were controlled by a metal mask. Finally, the PMMA layer 10 was removed with acetone and dried at 80° C. in a convection oven. The finished device is depicted schematically in FIG. 2(d); and a cross-sectional FESEM image is shown in FIG. 2(h). Note particularly the spaces between adjacent nanowires to facilitate gas transport.

EXAMPLE 12

Basic I-V Characteristics for Various Sensor Arrays

Figure 3:
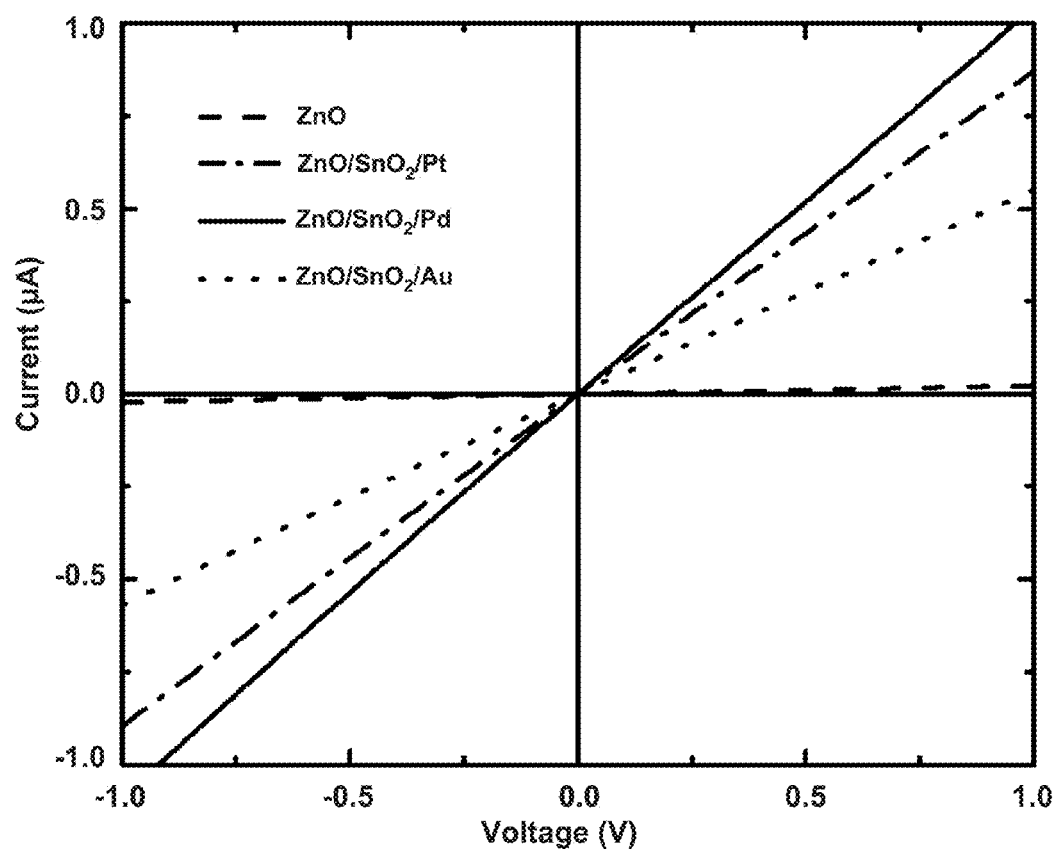
FIG. 3 depicts basic I-V characteristics for various sensor arrays ($ZnO/SnO_2/Pd$, $ZnO/SnO_2/Pt$, and $ZnO/SnO_2/Au$).

FIG. 3 depicts measured basic I-V characteristics for various sensor arrays (ZnO/$SnO_2$/Pd, ZnO/$SnO_2$/Pt, and ZnO/$SnO_2$/Au) in dry air at room temperature after loading into the sensor testing system. For comparison, measurements were also taken on pristine ZnO nanowire arrays, prepared following the same fabrication procedures, but without the noble metal nanoparticle coatings. The highly linear I-V plots indicated that the contacts between electrodes and nanowires were all ohmic.

The resistance of the pristine ZnO devices was almost 20 times higher than that of the coated nanowire array sensors. From this observation we inferred that in the coated nanowires most of the current flowed through the shell nanoparticle layer, with the core ZnO nanowires acting primarily as structural templates rather than as electrically conductive channels. In further experiments, the pristine ZnO device showed only limited sensitivity as compared with $SnO_2$/noble metal coated devices, implying that the ZnO nanowire and seed layers were not, directly, major contributors to the sensitivity of the devices.

EXAMPLE 13

Proposed Mechanism

Figure 4A:
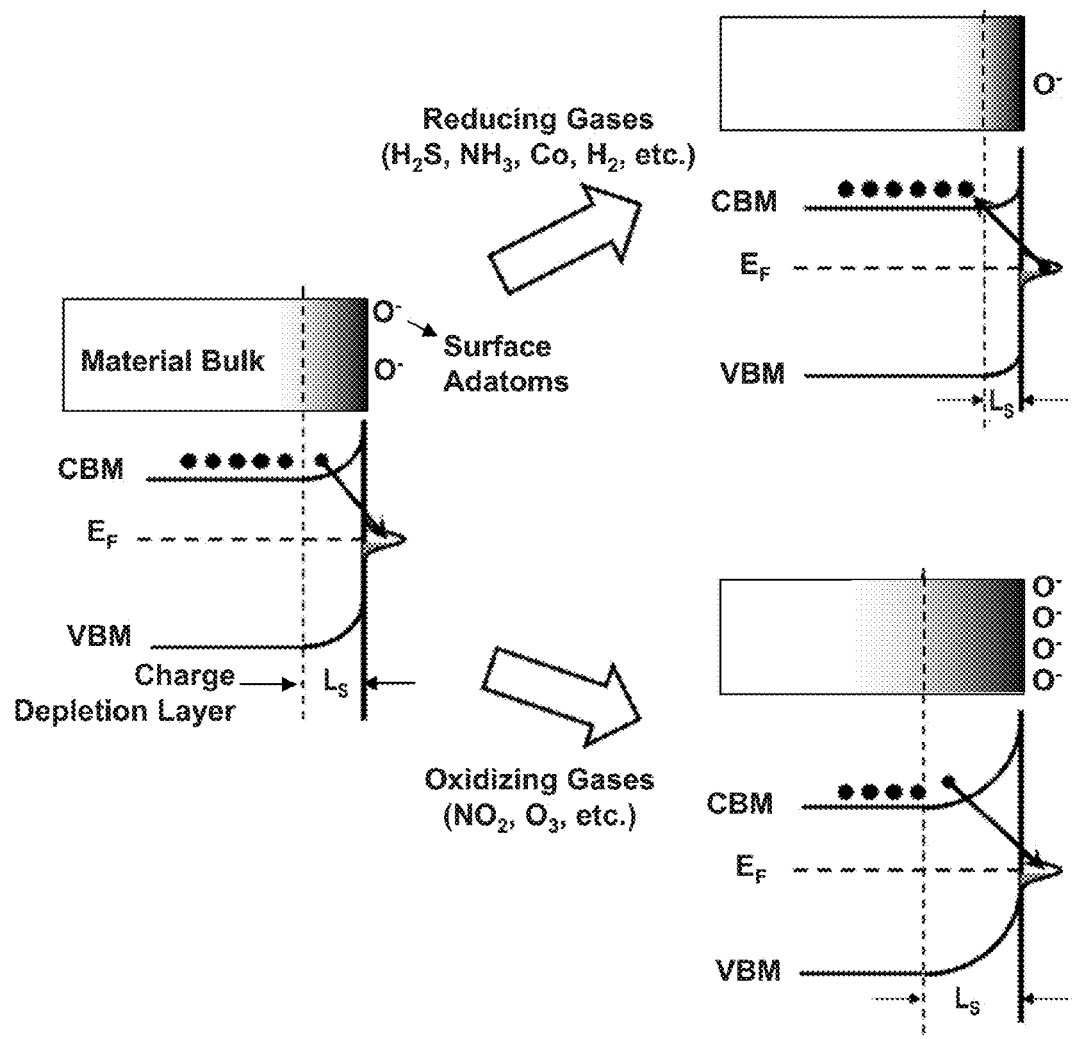
FIG. 4(a) depicts schematically the change in width of the space charge layer, $L_s$, in energy bands near the surface of an n-type metal oxide—before and after exposure to a reducing gas or an oxidizing gas.

Without wishing to be bound by this hypothesis, we propose that the sensing responses of metal oxide conductometric gas sensors may be explained by oxygen absorption and desorption on the metal oxide surfaces. FIG. 4(a) depicts schematically the change in width of the space charge layer, $L_s$, in energy bands near the surface of an n-type metal oxide—before and after exposure to a reducing gas or an oxidizing gas. Before exposure to a test gas, oxygen from the atmosphere is adsorbed onto the metal oxide surface as "adatoms" ($O^-$, $O^{2-}$, $O_2^-$, etc.):

$$O_2 + e^- \rightarrow nO^- (\text{or } O^{2-}, O_2^-, \text{etc.})$$

These adatoms on the surface trap electrons from the n-type metal oxides, forming a carrier depletion layer. The carrier depletion layer decreases the cross-section of the effective conduction channel in the bulk material, and increases the inter-particle energy barriers, thus reducing the conductivity of the n-type metal oxides. Reducing gases ($H_2S$, $NH_3$, CO, etc.) can react with the adsorbed oxygen adatoms, causing electrons to be released back to the metal oxides, with a resulting increase in electrical conductance, e.g.:

$$H_2 + O^- \rightarrow H_2O + e^-$$

$$CO + O^- \rightarrow CO_2 + e^-$$

$$2NH_3 + 3O^- \rightarrow 3H_2O + N_2 + 3e^-$$

$$H_2S + 3O^- \rightarrow H_2O + SO_2 + 3e^-$$

By contrast, oxidizing gases such as $NO_2$ decrease the conductance by trapping more electrons from the n-type metal oxides, e.g.:

$$NO_2 + e^- \rightarrow NO_2^-$$

Therefore, the novel device makes it relatively easy to discriminate oxidizing gases from reducing gases, simply by monitoring whether the conductance decreases or increases, respectively. The novel device is capable of much finer discrimination than that, however, more than just distinguishing oxidizing gases from reducing gases. The novel device can also respond to gases that are neither oxidizing nor reducing, although in most cases the response will not be as strong.

EXAMPLES 14-28

Responses of Three Noble Metal Nanoparticle-Coated Detectors to Five Gases

Figure 4B:
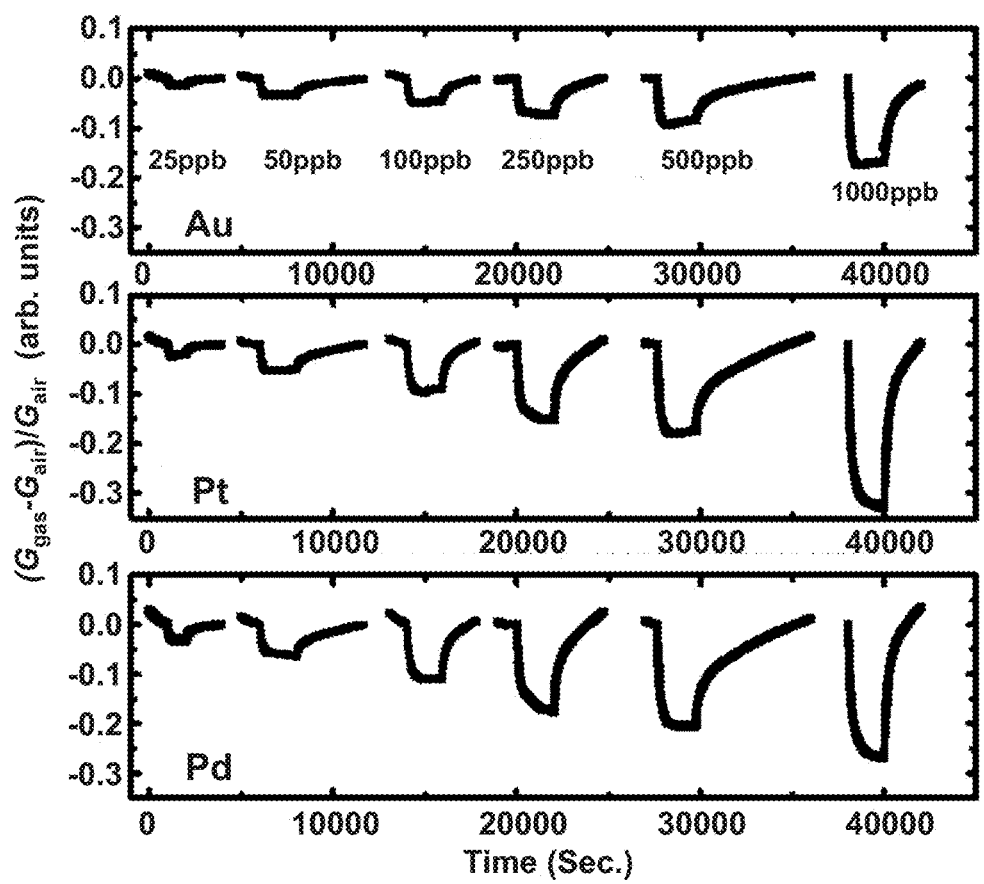
FIGS. 4(b) through 4(f) depict responses of three different noble metal nanoparticle-coated nanowire detectors to, respectively, diluted $NO_2$, $H_2S$, $NH_3$, CO, and $H_2$.
Figure 4C:
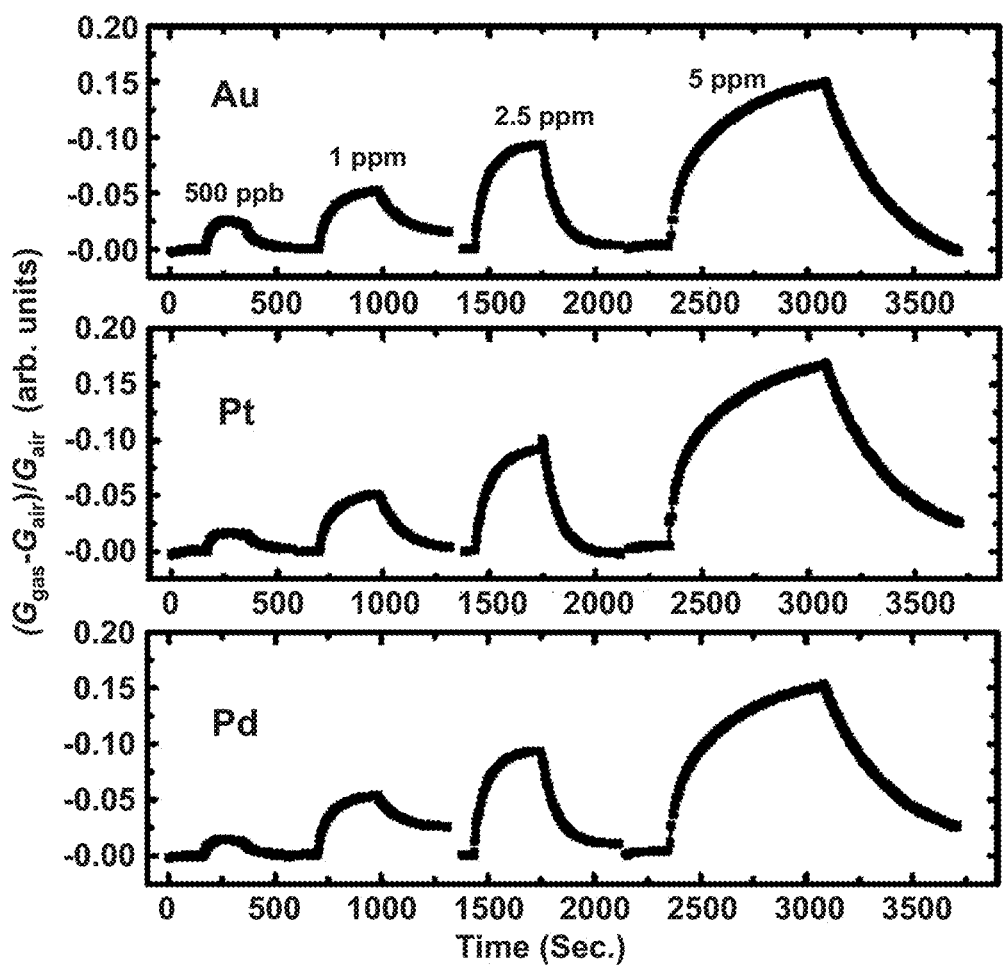
Figure 4D:
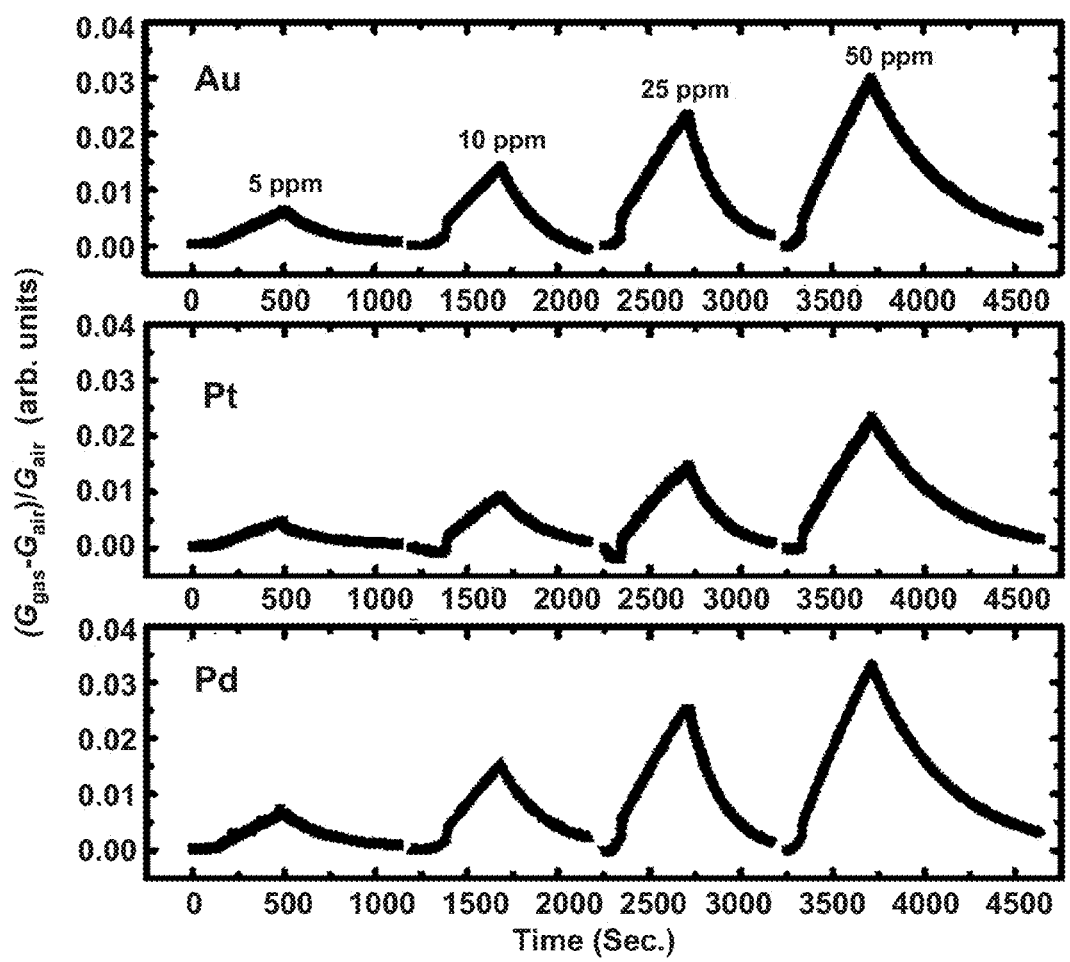
Figure 4E:
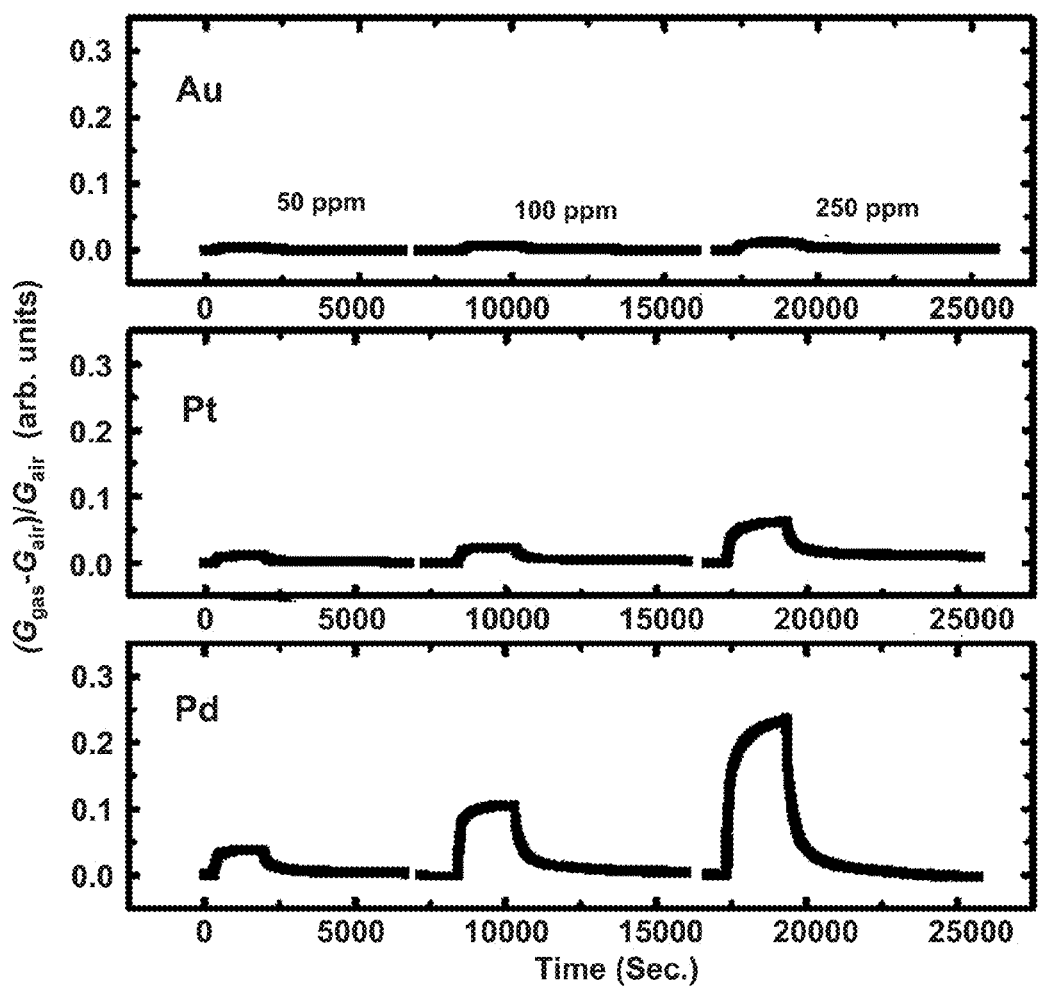
Figure 4F:
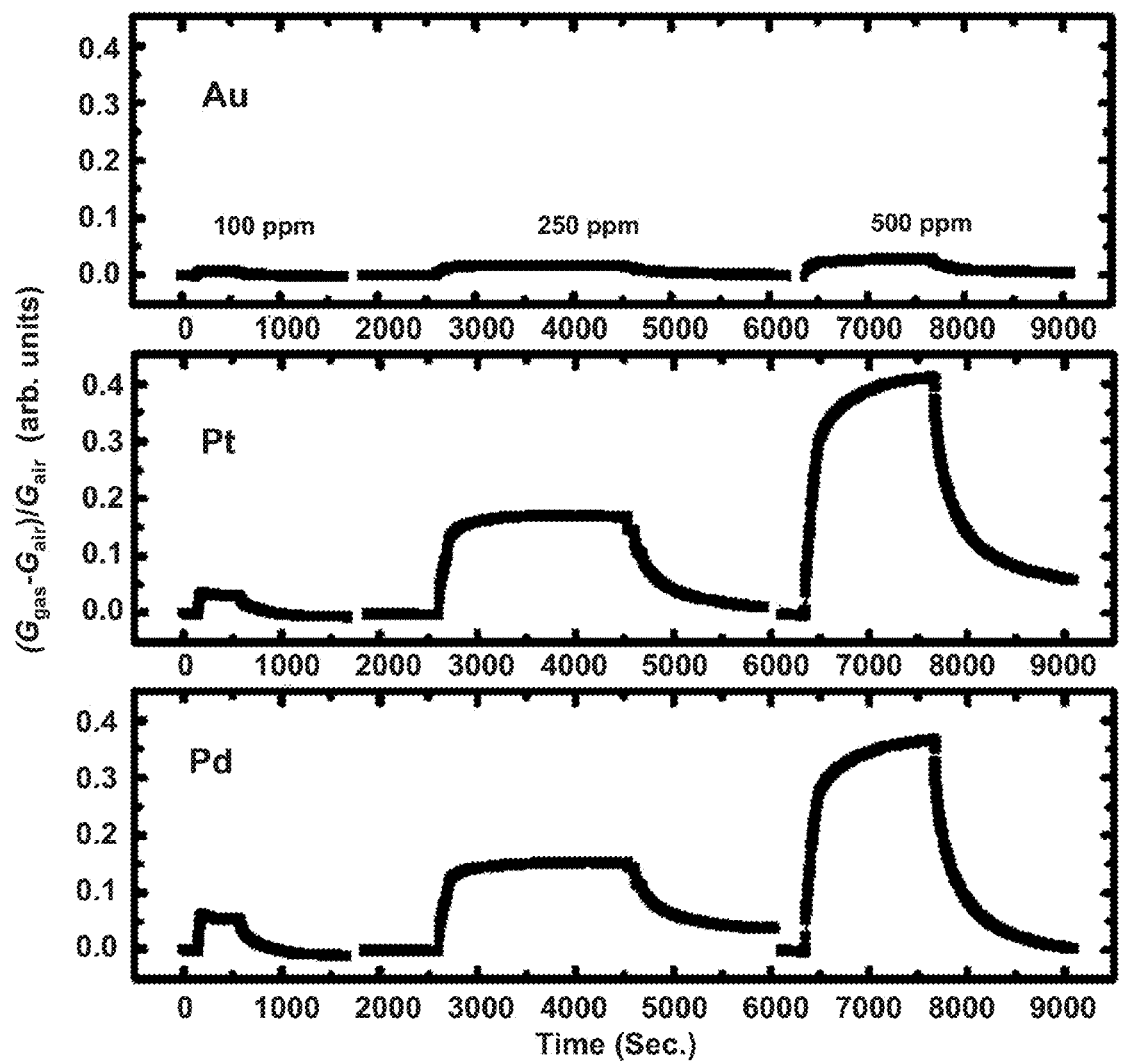

We measured responses at room temperature with three different noble metal nanoparticle-coated nanowire detectors with various concentrations of room-temperature, air-diluted $NO_2$ (FIG. 4(b)), $H_2S$ (FIG. 4(c)), $NH_3$ (FIG. 4(d)), CO (FIG. 4(e)), and $H_2$ (FIG. 4(f)), of different concentrations at room-temperature. Each plot shows normalized sensing responses, ($G_{gas} - G_{air}$)/$G_{air}$, where the un-normalized Gs have arbitrary units. The prototype devices showed high sensitivity to $H_2S$ and $NO_2$, with detection limits of 500 ppb and 25 ppb, respectively. The response speed, measured as the duration from the initial gas input until the time 90% of the ultimate sensing response was reached, was estimated as about 10~15 minutes. The devices gave a positive change in conductance to reducing gases, and a negative change in conductance for the oxidizing gas. $NH_3$ was detected at a detection limit of 5 ppm.

It has previously been difficult to detect CO and $H_2$ at room temperature with metal oxide conductometric sensors. However, the prototype novel device successfully detected air-diluted CO and $H_2$ at room temperature. Without wishing to be bound by this hypothesis, we believe that the successful detection of CO and $H_2$ can be ascribed, at least in part, to the large surface area of the nanowire arrays and the catalytic effect of the noble-metal decorations. CO and $H_2$ responded differently to different noble metals, meaning that the noble metals not only enhance sensitivity, but that the differing responses may be used to discriminate between different species, i.e., to enhance selectivity between different types of gases.

EXAMPLES 29 AND 30

Statistical Methods; Two- and Three-Dimensional Principal Components Analysis

One way to increase discrimination between or among different analytes is to construct a knowledge database for various gases, i.e., a collection of "smell prints." Various statistical methods known in the art may be used to identify and analyze correlations and differences in the response data for sensor arrays. Among these methods are principal component analysis, partial least squares, multiple linear regression, principal component regression, and discrimination function analysis. Principal component analysis is a preferred method for analyzing and displaying the responses of a sensor array, because it is linear, it is "unsupervised," it requires little or no a priori knowledge, and in most cases, only response variables are needed (e.g. response strength and speed). As a practical matter, it can be difficult to plot response vectors when more than three response variables are used. However, principal component analysis can reduce the effective dimensionality of the response data, while preserving the majority of the information by using covariance analysis.

Figure 5A:
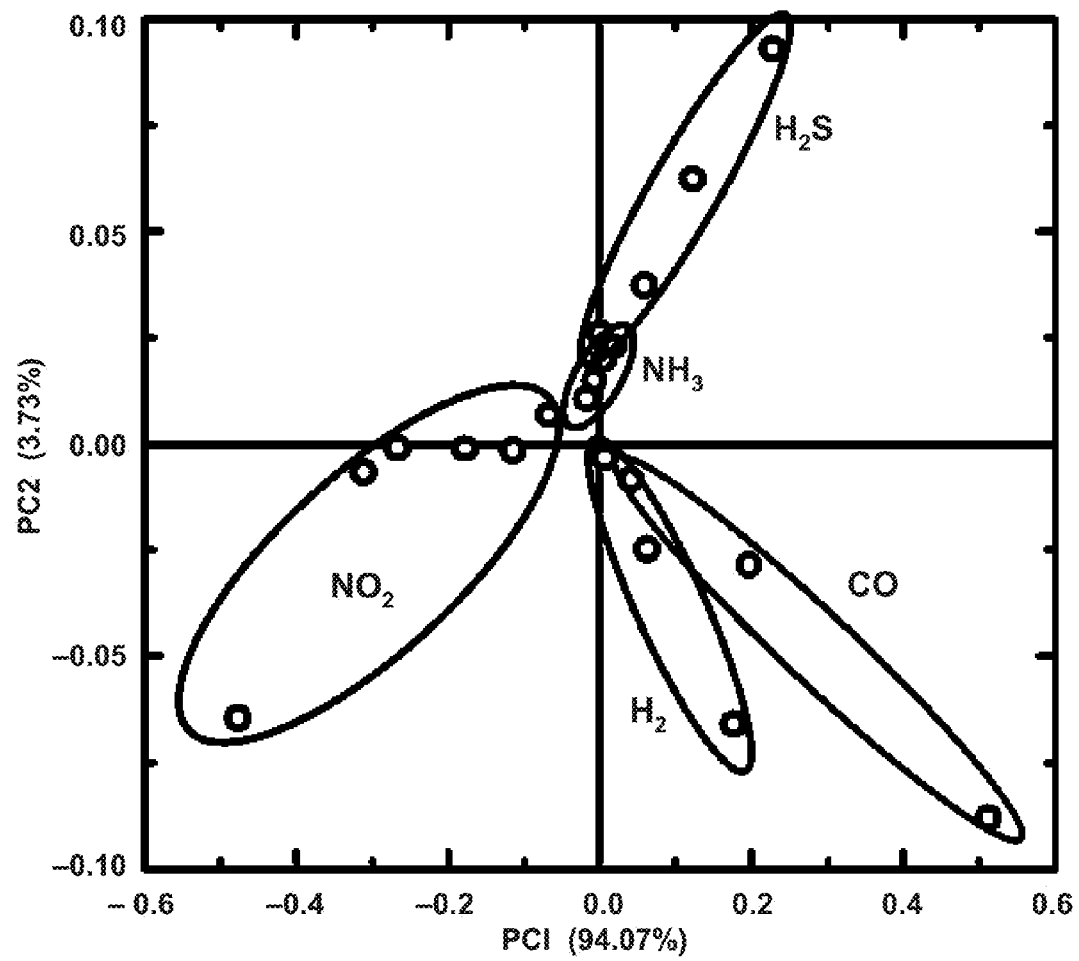
FIG. 5(a) depicts a plot of the first two principal components in a principal components analysis of the responses of a prototype array to five dilute gases.

The data acquired by the sensor array were represented by a response matrix $R_{m \times n}$. Each column of R corresponds to a particular gas (at a specific concentration), while the rows were the responses for a sensor device for different measurements. We first considered the response strengths as the variables for principal component analysis. Since there were three independent sensors (in this prototype), each column in the response matrix corresponded to a vector in three-dimensional space. Using a self-programmed principal component analysis code that conducts singular value decomposition, the three-dimensional data were projected onto a two-dimensional principal component space. The plot in the first two principal components is illustrated in FIG. 5(a). The cumulative variance of the principal components (PC1 and PC2) was 98.80%, indicating that the two-dimensional diagram had abstracted nearly all the information from the raw three-dimensional data. Data points were grouped into clusters, based on the types of gases tested. In general, the clusters were well-separated, meaning that the sensor array could discriminate well among these compounds, although there were small areas of overlap. $NO_2$, $H_2$, and CO each had distinct response trends as the concentration increased. On the other hand, $H_2S$ and $NH_3$ shared similar changes in direction, making it more difficult to distinguish $H_2S$ from $NH_3$. Also, the clusters for CO and $H_2$ overlapped at lower concentrations, introducing some ambiguities in those regimes also.

Figure 5B:
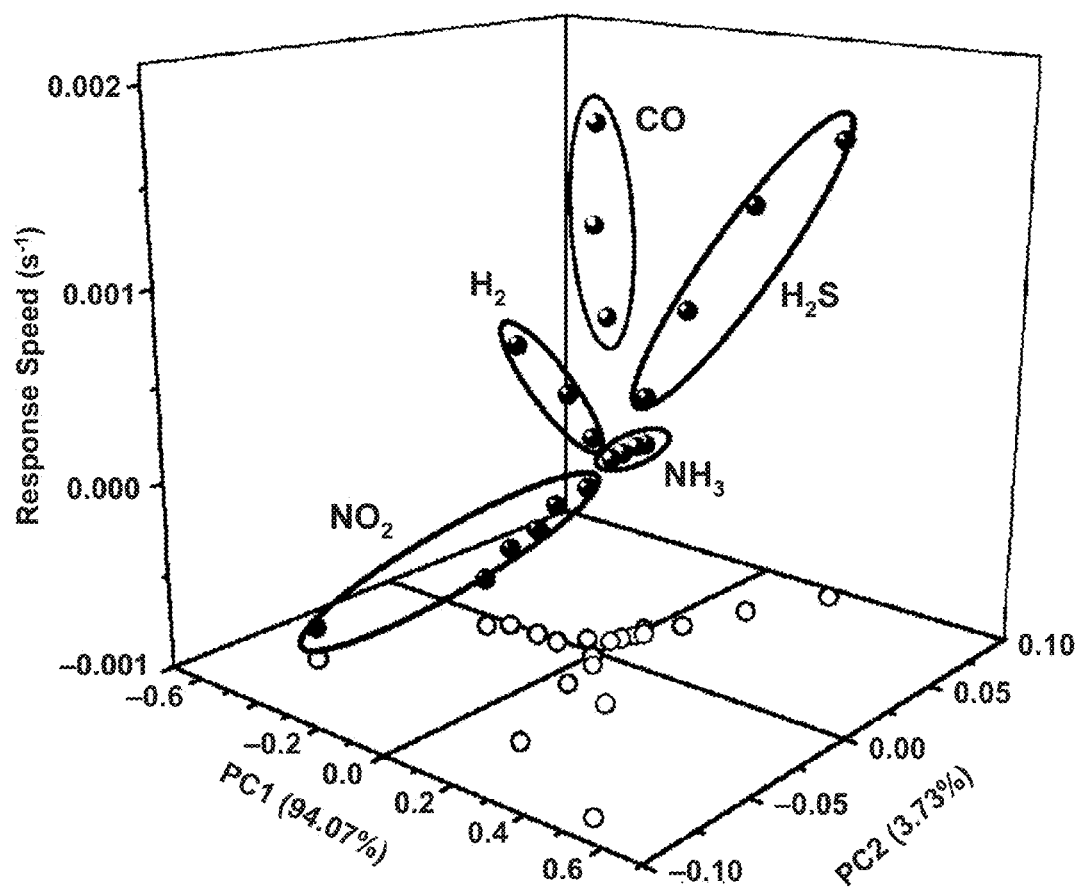
FIG. 5(b) depicts a three-dimensional principal components plot that also included response speeds.

The gas sensors showed different response speeds to different gases; the measured response times can themselves be used to discriminate between different gases. For example, FIG. 5(b) depicts a three-dimensional principal components plot that also includes response speeds (measured as the slope of the response curve immediately following initial exposure to the gas). As compared to FIG. 5(a), discrimination is significantly enhanced in FIG. 5(b) by also incorporating data on response speed. No overlaps were seen between any of the clusters, and all clusters tended to change along different directions. Note, for example, that by contrast to FIG. 5(a), in FIG. 5(b) $H_2S$ and $NH_3$ are well resolved from one another. This enhancement of selectivity can be ascribed to the different absorption and desorption dynamics for different gases.

EXAMPLE 31

Alternative Embodiments Employing Other Metal Nanoparticles

Another method to increase the selectivity of sensor array is to include more sensors built with new materials. Any of the noble metals may be used in forming such an array; in general, the more different metals are contained in the array, the greater will be its powers of discrimination. The noble metals include ruthenium, rhodium, palladium, silver, osmium, iridium, platinum, and gold. The noble metals are preferred due to their sensitivity. However, other metals besides the noble metals may also be used in practicing the invention.

EXAMPLE 32

Alternative Embodiments Employing Other Metal Oxide Nanowires

A preferred material for forming the nanowires is ZnO, due to its ease of fabrication. Alternatively, other materials known in the art for preparing nanowires may be used, such as CuO, $SnO_2$, or $TiO_2$.

EXAMPLES 33 AND 34

Alternative Embodiments Employing $In_2O_3$ or $WO_3$ Nanoparticles

Figure 6A:
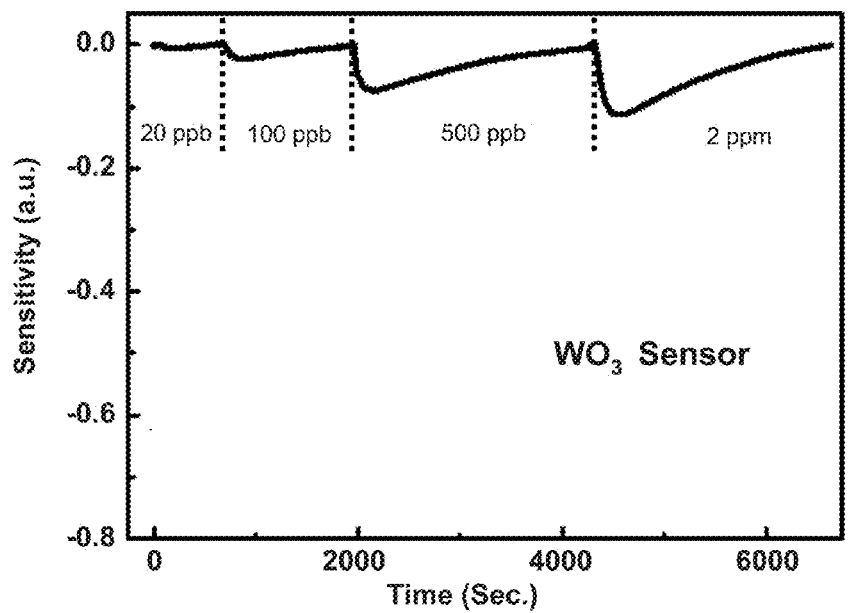
FIGS. 6(a)-(c), 7(a)-(c), 8(a)-(c), 9(a)-(c), and 10(a)-(c) depict measurements made with $WO_3$-coated nanowires, $In_2O_3$-coated, and $SnO_2$-coated nanowires.
Figure 6B:
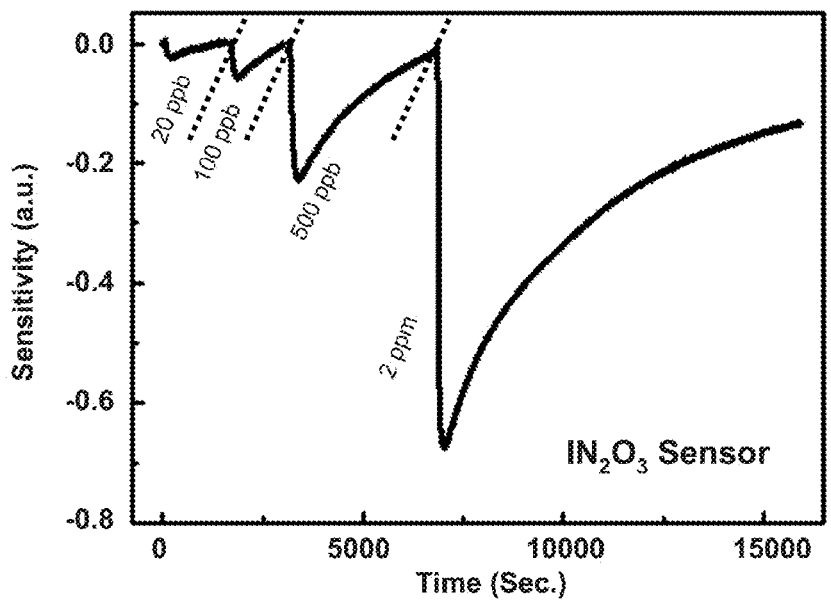
Figure 6C:
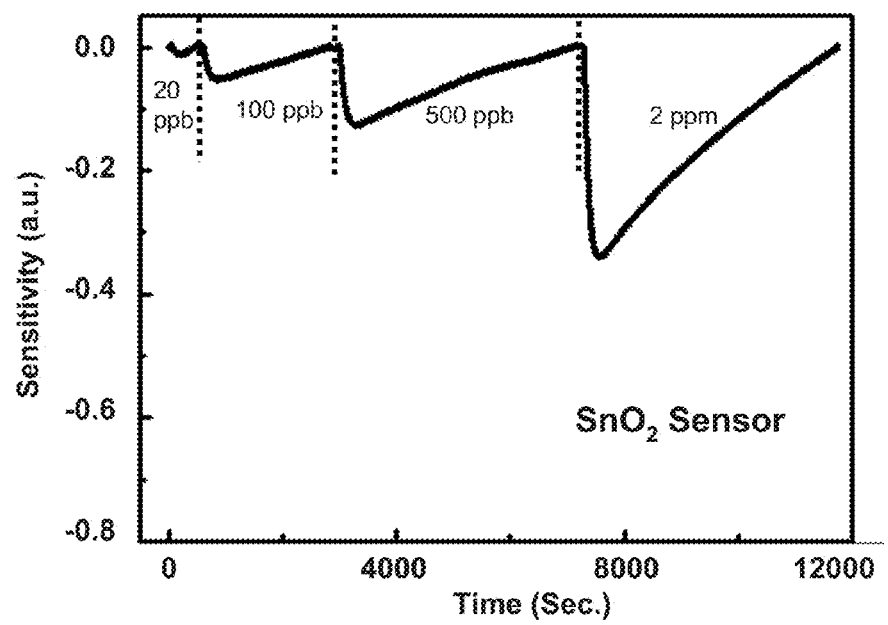
Figure 7A:
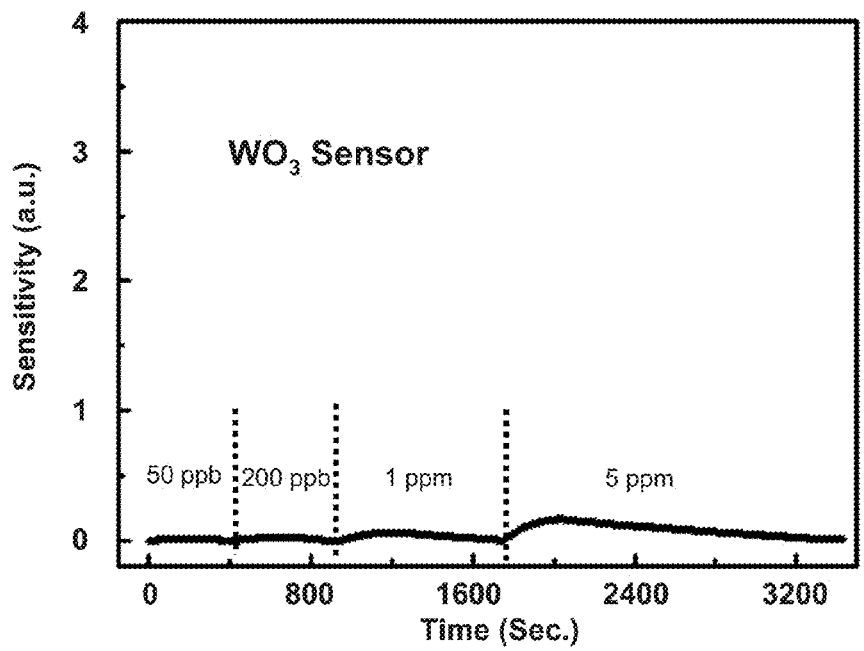
Figure 7B:
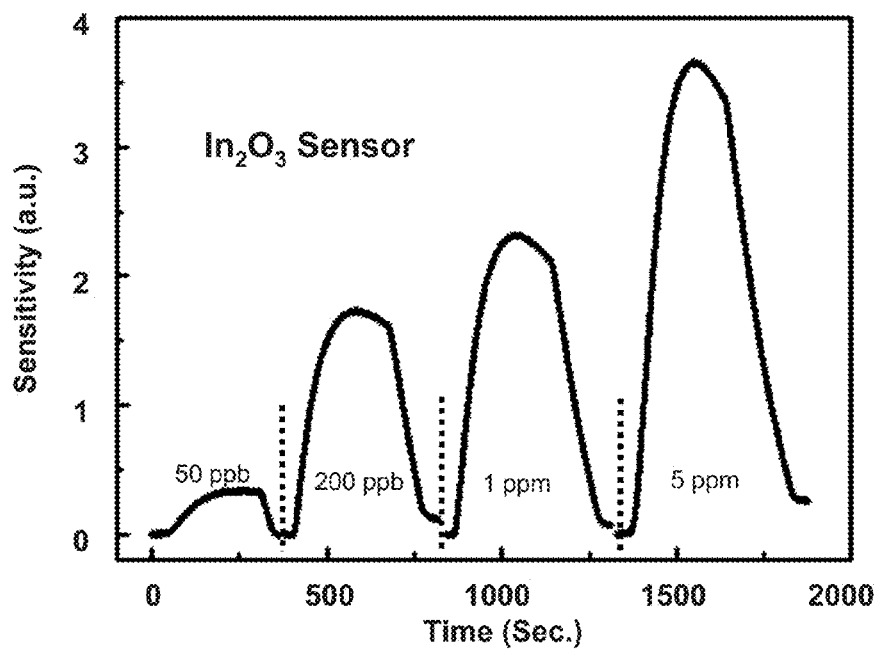
Figure 7C:
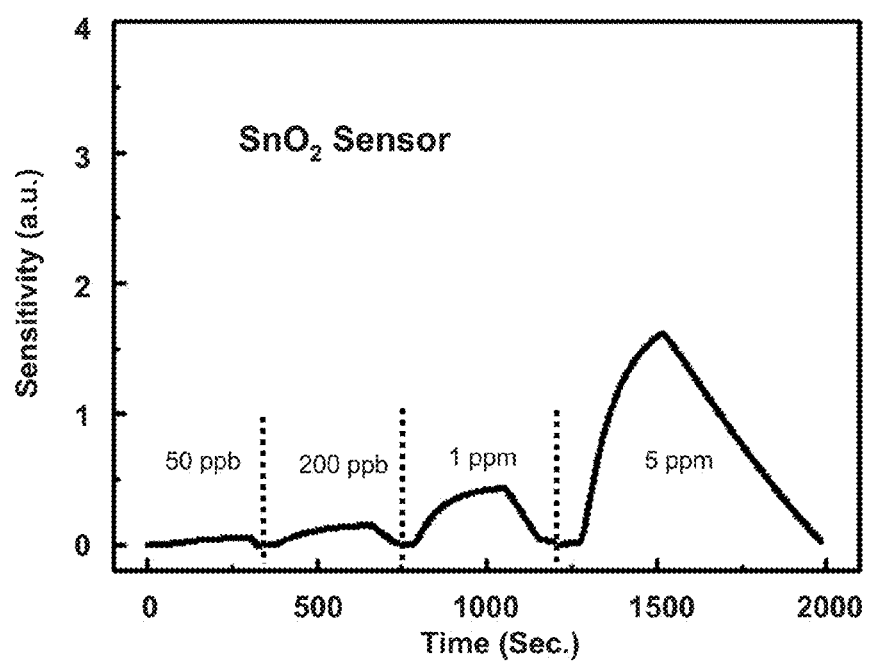
Figure 8A:
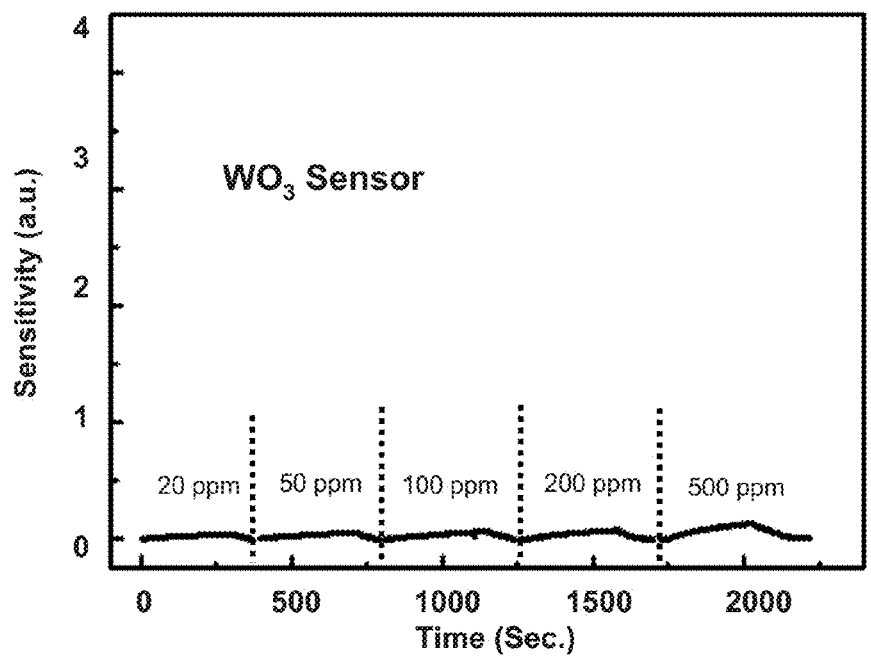
Figure 8B:
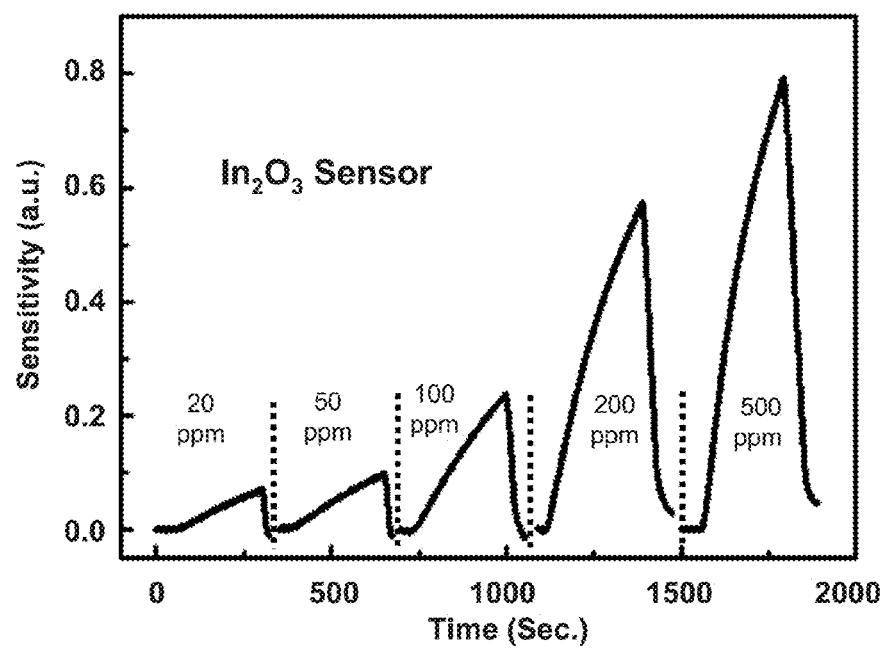
Figure 8C:
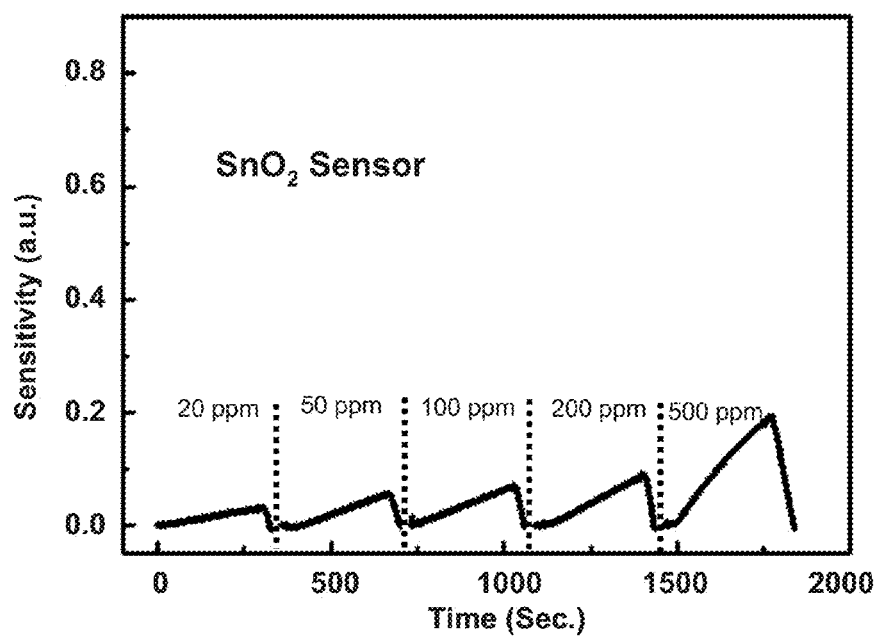
Figure 9A:
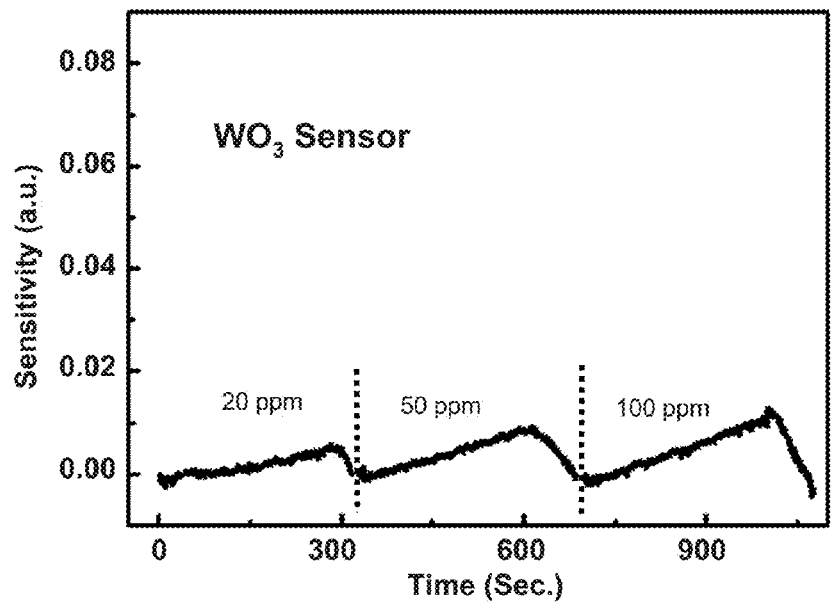
Figure 9B:
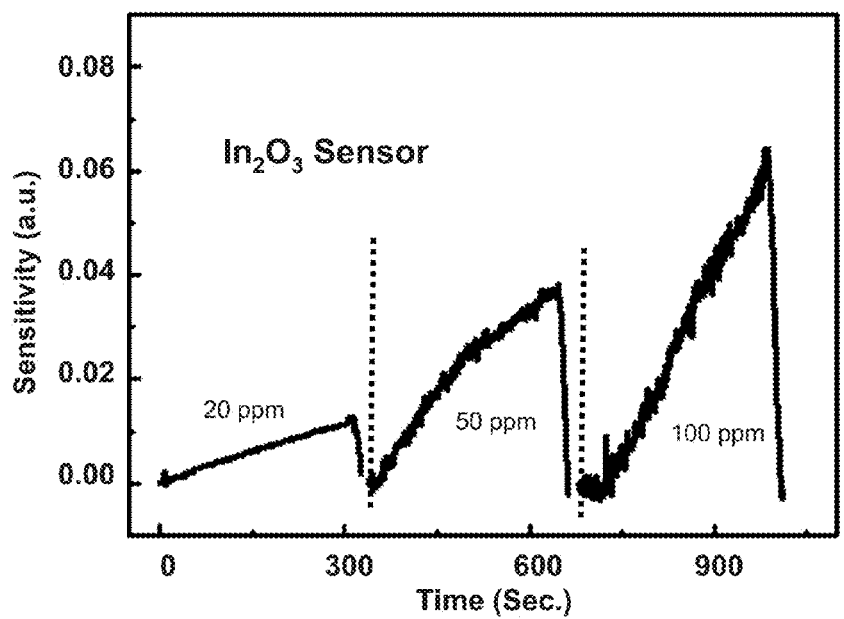
Figure 9C:
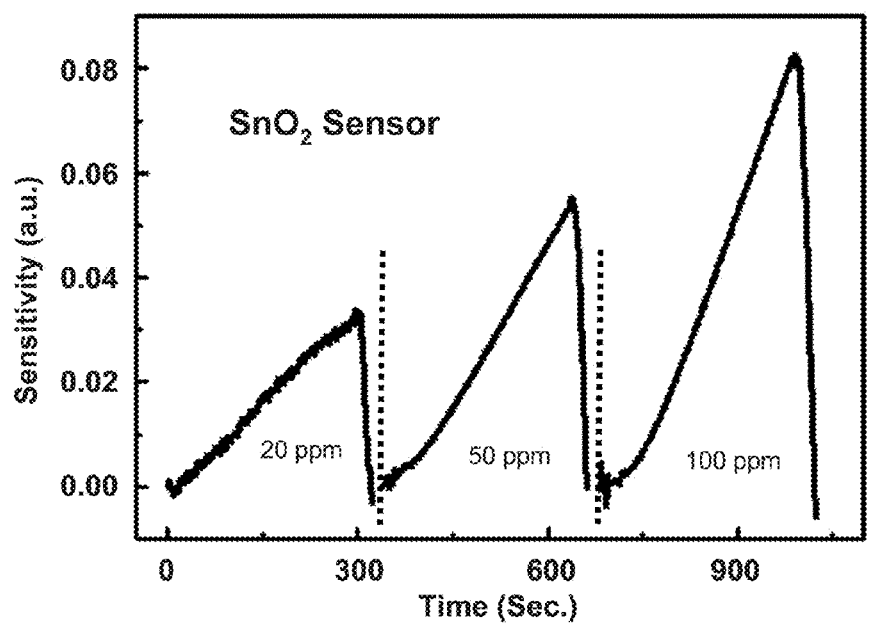
Figure 10A:
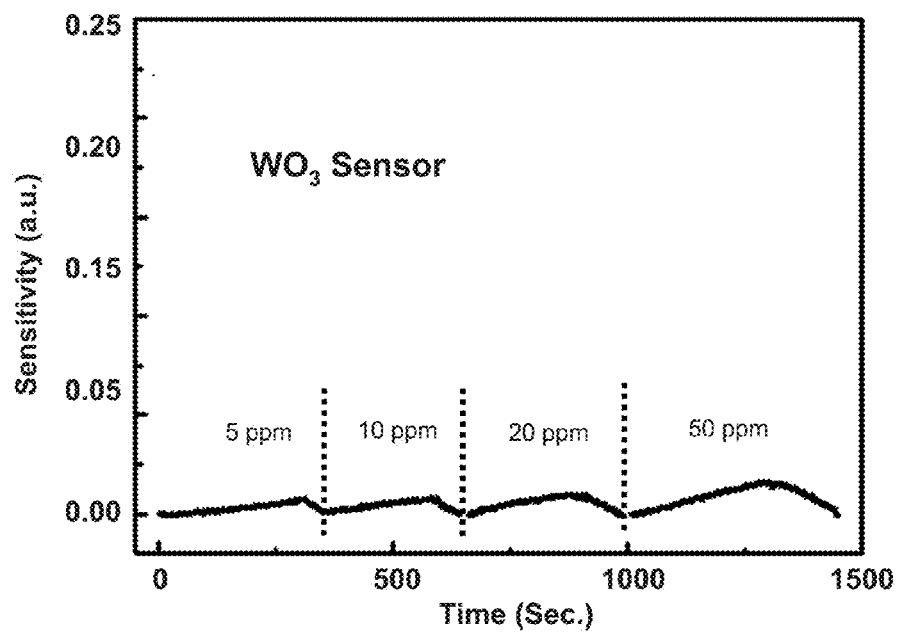
Figure 10B:
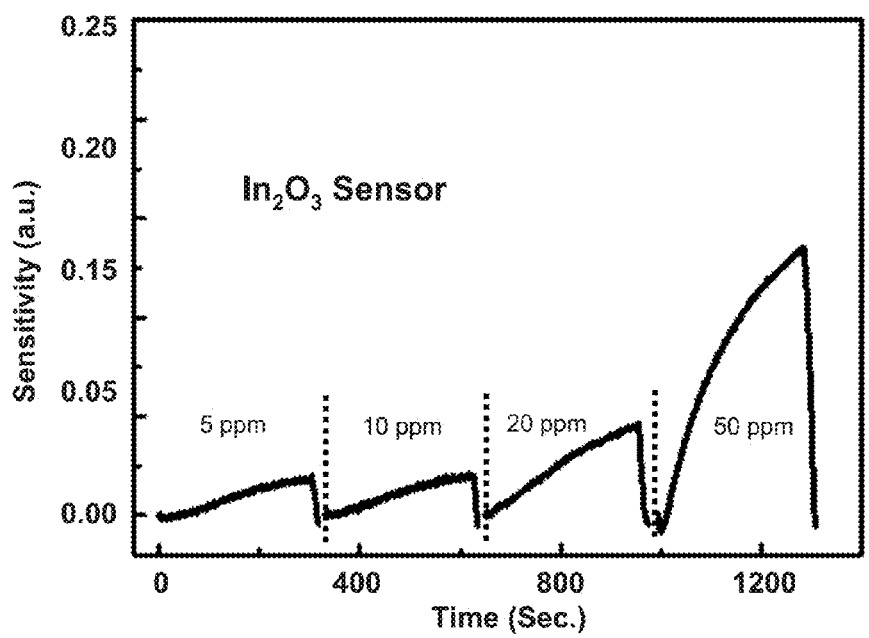
Figure 10C:
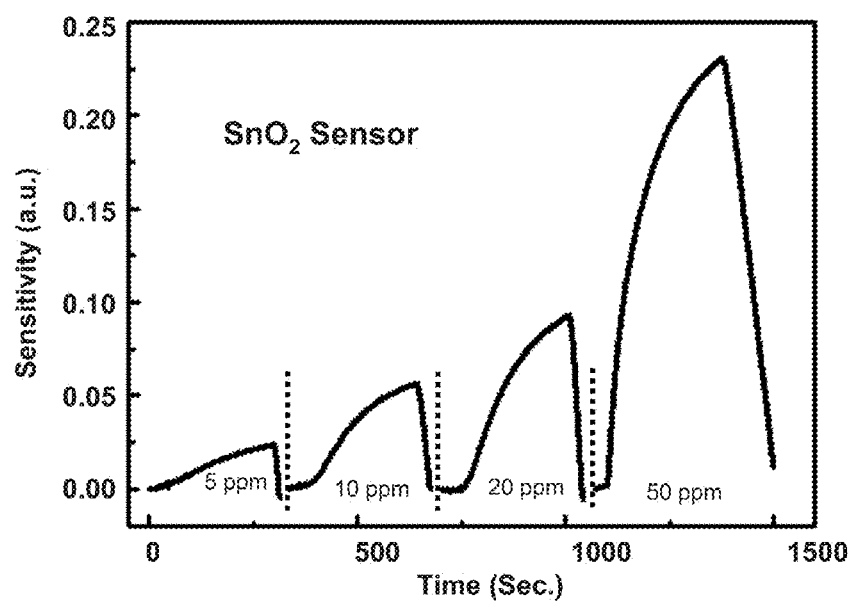

To test alternative prototype embodiments of the invention, arrays were prepared as otherwise described above, but in place of the $SnO_2$ either $In_2O_3$ or $WO_3$ was sputtered onto the ZnO nanowire array surface. $SnO_2$ was also used for comparison. (Noble metals were not used in these experiments.) We measured the responses of the arrays to $H_2S$, $NO_2$, CO, $NH_3$, and $H_2$. All measurements were taken at room temperature. Results are shown in FIGS. 6(a)-(c), 7(a)-(c), 8(a)-(c), 9(a)-(c), and 10(a)-(c). FIG. 6 depicts measurements for $NO_2$. FIG. 7 depicts measurements for $H_2S$. FIG. 8 depicts measurements for $H_2$. FIG. 9 depicts measurements for CO. FIG. 10 depicts measurements for $NH_3$. In each of FIGS. 6-10, part (a) depicts measurements made with the $WO_3$-coated nanowires, part (b) depicts measurements made with the $In_2O_3$-coated nanowires, and part (c) depicts measurements made with the $SnO_2$-coated nanowires. These sensors showed high sensitivities to $H_2S$ and $NO_2$, down to the part per billion (ppb) levels at room temperature. Again, the differing responses to differing materials provides a basis for discriminating between different gases through methods such as principal component analysis.

EXAMPLE 35

Alternative Embodiments Employing Other Metal Oxide Nanoparticles

Nanoparticles of other metal oxide may also be used in place of the $SnO_2$ nanoparticles to act as sensing materials, including as just a few of many examples $MoO_3$, $Ga_2O_3$, CuO, $Cu_2O$, NiO, $VO_2$, $V_2O_5$, $Fe_2O_3$, $Fe_3O_4$, $WO_3$, $In_2O_3$, or $TiO_2$.

EXAMPLE 36

Alternative Embodiments Employing Other Semiconductor Nanoparticles

The shell layer may comprise semiconductor nanoparticles other than, or in addition to metal oxide nanoparticles. Examples of semiconductors other than metal oxides that may be used in the shell layer include II-VI semiconductors (e.g., CdS, CdSe, CdTe, ZnS, ZnSe, ZnTe, HgCdTe, HgCdTe, HgZnSe), III-V semiconductors (e.g., AlSb, AlAs, AlN, AlP, BN, BP, BAs, $B_{12}As_2$, GaSb, GaAs, GaN, GaP, InSb, InAs, InN, InP, AlGaAs, InGaAs, InGaP, AlInAs, AlInSb, GaAsN, GaAsP, GaAsSb, AlGaN, AlGaP, InGaN, InAsSb, InGaSb, AlGaInP, InGaAsP, InGaAsSb, InAsSbP, AlInAsP, AlGaAsN, InGaAsN, InAlAsN, GaAsSbN, GaInNAsSb, GaInAsSbP), and other semiconductors known in the art. Techniques for coating semiconductor nanoparticles are well-known in the art and include methods such as thermal evaporation, pulsed laser deposition, sputtering, and metal-organic chemical vapor deposition.

EXAMPLE 37-39

Alternative Embodiments Employing a $GaN/Al_2O_3$ Substrate

The prototype examples described above were prepared on Si substrates. Other substrates known in the art may also be used, in lieu of Si. In an alternative embodiment, we prepared a ZnO nanowire array on a $GaN/Al_2O_3$ substrate. No intermediate Cr, Au, or amorphous ZnO layers were coated onto the substrate. The procedures used were otherwise generally as described in the preceding examples. Thus the overall fabrication process was simpler to implement. $In_2O_3$, $SnO_2$, or $WO_3$ nanoparticles were sputtered onto the ZnO nanowire arrays.

Figure 11A:
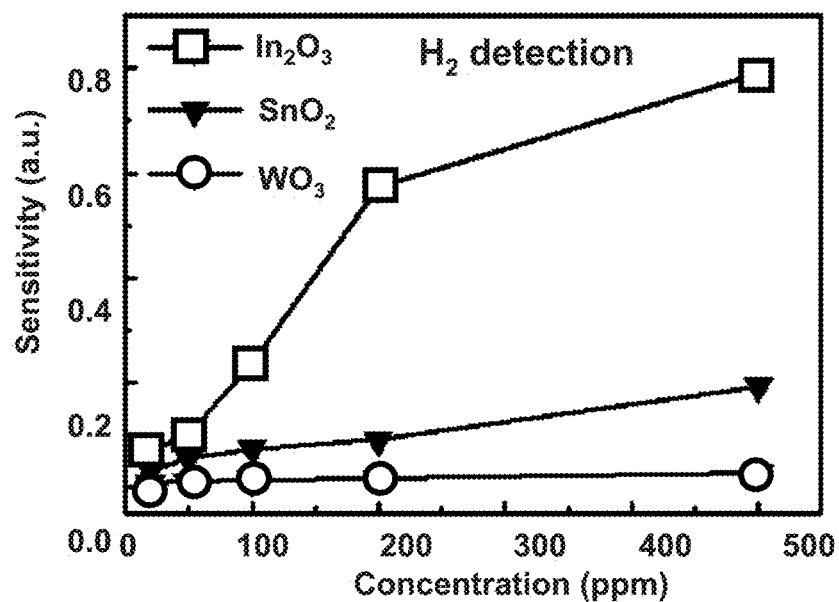
FIGS. 11(a)-(d) depict sensitivity of an array fabricated on a $GaN/Al_2O_3$ substrate.
Figure 11B:
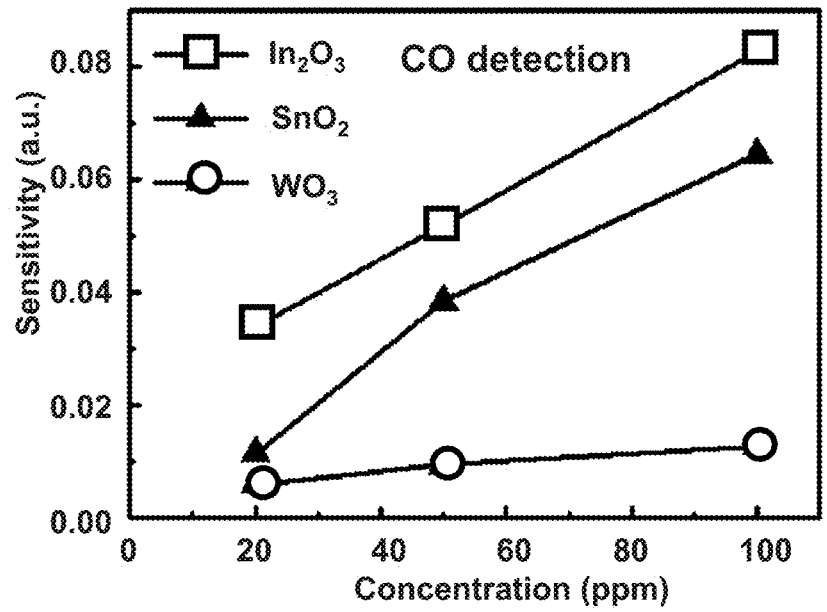
Figure 11C:
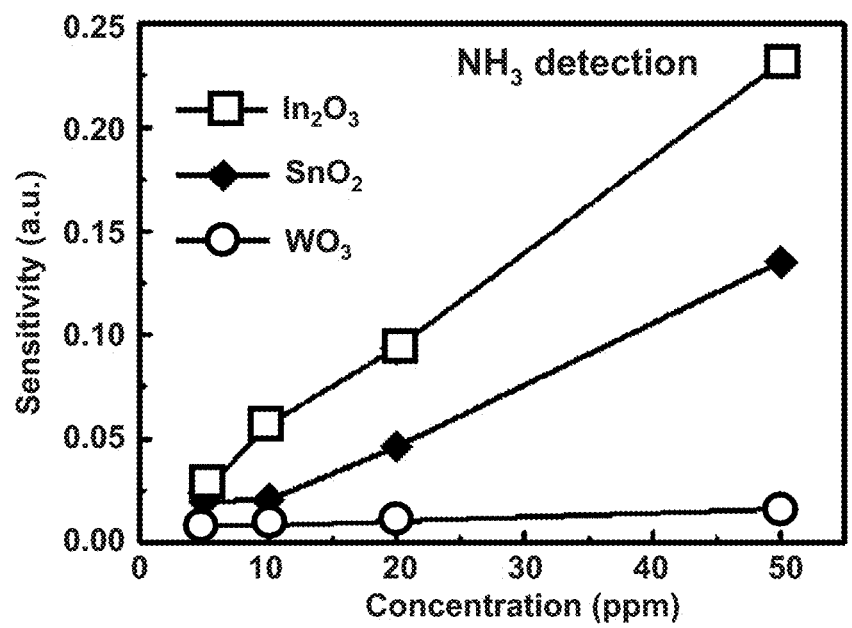
Figure 11D:
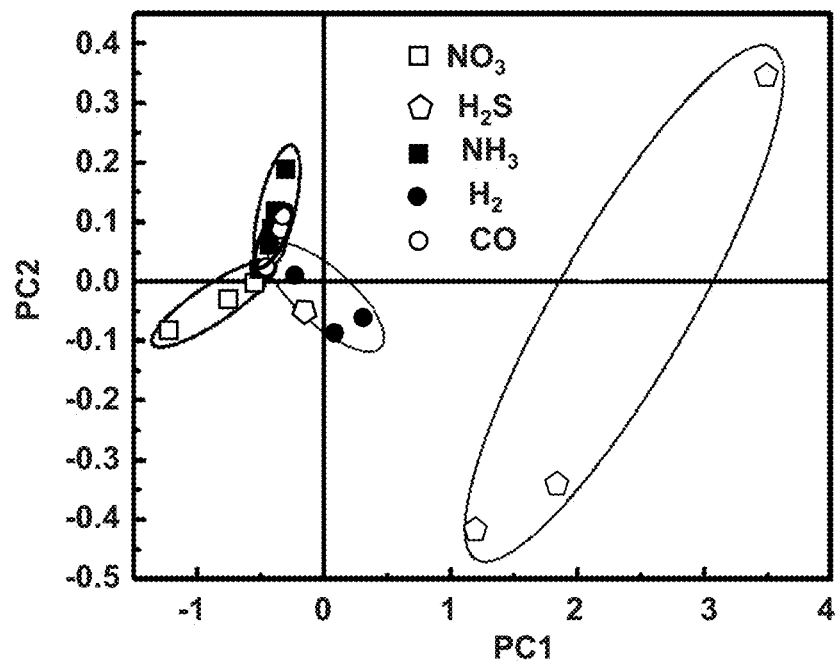

Sensitivity was measured towards $H_2$, CO, and $NH_3$ gases. Results are depicted in FIGS. 11(a)-(d). FIG. 11(a) depicts detection of $H_2$ with the three different metal oxide nanoparticle coatings. FIG. 11(b) depicts detection of CO. FIG. 11(c) depicts detection of $NH_3$. FIG. 11(d) depicts a principal component analysis of measurements with five gases. The sensing responses were different from those seen with a Si substrate, and the response profiles were different, although the two sets of sensors had similar detection limits. Compare FIGS. 5(a) and 11(d).

EXAMPLE 40

Alternative Embodiments and Preferred Ranges

Various alternative embodiments may be practiced in implementing the invention, and certain parameters may fall within a range of values or a preferred range without departing from the invention. Many of these alternatives have been described previously. Others include the following:

The array of nanowires should have at least 3 nanowires, preferably at least 10, more preferably at least 100.

The diameter D of each of the nanowires is from 10 nm to 100 µm; preferably from 50 nm to 50 µm; more preferably from 100 nm to 1 µm.

The height of the nanowires is from D to 100 D; preferably from 2 D to 50 D; more preferably from 5D to 20 D The distance between adjacent nanowires is from 10 nm to 50 D; preferably from 100 nm to 20 D; more preferably from 1 µm to 10 D.

The diameter of the semiconductor nanoparticles is from 1 nm to D; preferably from 5 nm to 0.5 D; more preferably from 10 nm to 0.1 D.

If noble metal nanoparticles are incorporated into the shell layer or adhere onto the shell layer, then the diameter of the noble metal nanoparticles is from 1 nm to D; preferably from 5 nm to 0.5 D; more preferably from 10 nm to 0.1 D.

The electrical resistance of a device in accordance with the invention is altered in the presence of a concentration of at least one reducing gas in air, or in the presence of a concentration of at least one oxidizing gas besides oxygen in air; as compared to the electrical resistance of the device in dry air in the absence of any reducing gas and in the absence of any oxidizing gas besides oxygen; wherein the alteration of the electrical resistance may be either an increase in the electrical resistance or a decrease in the electrical resistance of said device.

The electrical resistance would either remain unaltered in a comparison device; or the magnitude of the change in electrical resistance in the novel device would be at least twenty percent greater than the magnitude of the change in electrical resistance in a comparison device; when the electrical resistance of the two devices is measured under identical conditions; wherein the comparison device is otherwise identical to the novel device, except that the comparison device lacks a shell layer with semiconductor nanoparticles.

If noble metal nanoparticles are incorporated into the shell layer or adhere onto the shell layer, then the response of the electrical resistance of said device to at least one reducing gas in air, or to at least one oxidizing gas besides oxygen in air, is at least twenty percent greater than the magnitude of the change in electrical resistance of an otherwise identical device that lacks noble metal nanoparticles.

The dimensions and spacing of the nanowires and shell layer should be such as to permit the free flow of gases through the device, under the conditions in which it is to be used, wherein the resulting exchange time for gas to be exchanged from the interior of the device should not be substantially slower than the response time for the device to a particular gas that is to be detected.

The device preferably incorporates two electrodes, a first electrode and a second electrode; wherein the first electrode is in electrical contact with a first end of each of the nanowires; and the second electrode is in electrical contact with a second end of each of the nanowires; whereby the electrical resistance of the device may be determined by electrical resistance measurements made through the two electrodes.

A preferred embodiment is an article of manufacture that comprises more than one of the novel devices; wherein the chemical compositions of the different devices is different; and wherein the different devices exhibit different alterations in their electrical resistances in response to one or more gases, or the devices exhibit different response times as their electrical resistances alter in response to one or more gases, or both; whereby electrical resistance measurements made with the entire article of manufacture as a whole provide greater resolution to discriminate between the presence of different gases than is provided by electrical resistance measurements made with any of the individual devices alone.

The complete disclosures of all references cited in this specification; and the complete disclosure of the priority application, Ser. No. 61/387,540; and the complete disclosures of all references cited in priority application Ser. No. 61/387,540 are all hereby incorporated by reference in their entirety. In the event of an otherwise irreconcilable conflict, however, the present specification shall control.

We claim:

1. A device comprising:
    (a) an array comprising at least three wires; wherein said wires are aligned or approximately aligned with one another; wherein the diameter D of each of said wires is between 10 nm and 100 µm; wherein the height of each of said wires is between D and 100 D; and wherein the distance between adjacent wires is between 10 nm and 50 D;
    (b) a shell layer comprising semiconductor nanoparticles adhering to the surface of said wires; wherein the chemical composition of said semiconductor nanoparticles differs from the chemical composition of said wires, and the diameter of said semiconductor nanoparticles is between 1 nm and D; wherein said semiconductor nanoparticles comprise $SnO_2$, $MoO_3$, $Ga_2O_3$, $CuO$, $Cu_2O$, $NiO$, $VO_2$, $V_2O_5$, $Fe_2O_3$, $Fe_3O_4$, $WO_3$, or $In_2O_3$; and wherein said semiconductor nanoparticles additionally comprise at least one II-VI semiconductor or at least one III-V semiconductor;
    (c) a first electrode and a second electrode; wherein said first electrode is in electrical contact with a first end of each of said wires; and said second electrode is in electrical contact with a second end of each of said wires; whereby the electrical resistance of said device is determinable by electrical resistance measurements made through said first and second electrodes;
wherein:
    (d) one or more gases are present in the spacing between said wires, and the dimensions and spacing of said wires and said shell layer permit the free flow of the gases through said device; and
    (e) the electrical resistance of said device is altered in the presence of at least one reducing gas in air, or at least one oxidizing gas besides oxygen in air; as compared to the electrical resistance of said device in dry air in the absence of any reducing gas and in the absence of any oxidizing gas besides oxygen; wherein the alteration of the electrical resistance is either an increase or a decrease in the electrical resistance of said device.

2. The device of claim 1, additionally comprising noble metal nanoparticles within or adhering to said shell layer.

3. An article of manufacture comprising a plurality of devices as recited in claim 1; wherein the chemical compositions of said devices differ from one another; and wherein said devices exhibit differences from one another in one or both of the following characteristics: the alterations in electrical resistance in response to one or more gases, or the response time as electrical resistance alters in response to one or more gases; whereby electrical resistance measurements made with said article of manufacture provide greater resolution to discriminate between the presence of different gases than is provided by electrical resistance measurements made with any of the individual said devices.

* * * * *